United States Patent
Lieberman et al.

(10) Patent No.: US 7,736,003 B2
(45) Date of Patent: Jun. 15, 2010

(54) DIAGNOSIS AND TREATMENT OF DISORDERS OF THE EYE

(75) Inventors: David M. Lieberman, New York, NY (US); Jonathan Grierson, Atwater, OH (US)

(73) Assignee: Scientific Optics, Inc., La Jolla, CA (US)

( * ) Notice: Subject to any disclaimer, the term of this patent is extended or adjusted under 35 U.S.C. 154(b) by 0 days.

(21) Appl. No.: 12/305,279

(22) PCT Filed: Sep. 28, 2007

(86) PCT No.: PCT/US2007/021045
§ 371 (c)(1),
(2), (4) Date: Mar. 17, 2009

(87) PCT Pub. No.: WO2008/042314
PCT Pub. Date: Apr. 10, 2008

(65) Prior Publication Data
US 2009/0303441 A1    Dec. 10, 2009

Related U.S. Application Data

(60) Provisional application No. 60/827,344, filed on Sep. 28, 2006, provisional application No. 60/862,073, filed on Oct. 19, 2006, provisional application No. 60/885,504, filed on Jan. 18, 2007, provisional application No. 60/913,557, filed on Apr. 24, 2007.

(51) Int. Cl.
A61B 3/00    (2006.01)
A61B 3/10    (2006.01)
A61B 18/18   (2006.01)

(52) U.S. Cl. .............................. 351/246; 351/212; 606/5

(58) Field of Classification Search ................. 351/205, 351/206, 212, 246; 606/4, 5, 166
See application file for complete search history.

(56) References Cited

U.S. PATENT DOCUMENTS 6,416,179 B1 *  7/2002  Lieberman et al. .......... 351/212
6,599,285 B1 *  7/2003  Lieberman et al. ............. 606/5
6,669,342 B2   12/2003  Lieberman et al.

OTHER PUBLICATIONS

International Search Report and Written Opinion of International Application No. PCT/US07/21045 (filed: Sep. 28, 2007), dated Jul. 25, 2008.

* cited by examiner

*Primary Examiner*—Jack Dinh
(74) *Attorney, Agent, or Firm*—Kaplan Gilman & Pergament LLP

(57) ABSTRACT

Certain disorders of the cornea exhibit unique characteristics in a surface model of the cornea. Through various manipulations of the characteristics of the surface model of a patient's cornea, certain "markers" that are associated with disorders of the eye may be revealed.

26 Claims, 41 Drawing Sheets

Regular Astigmatism

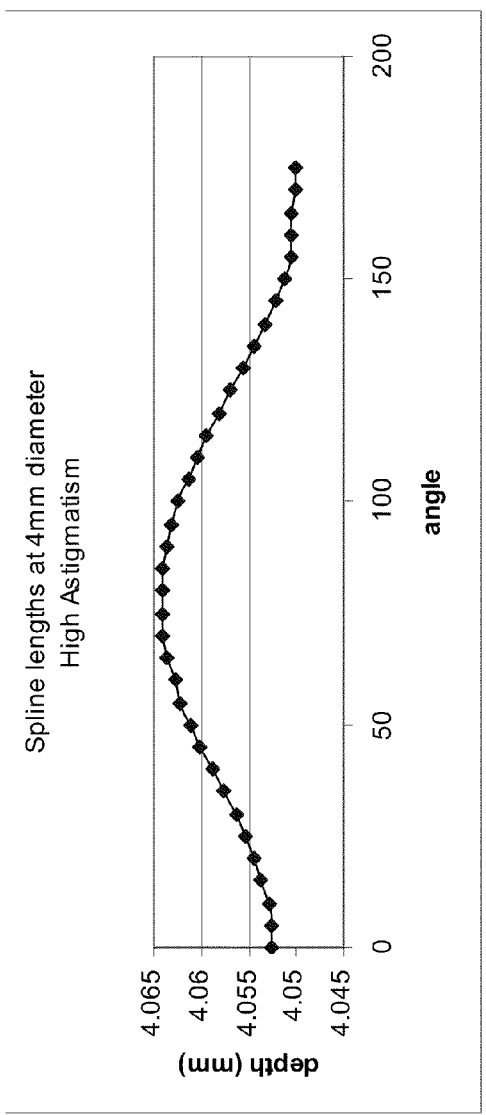
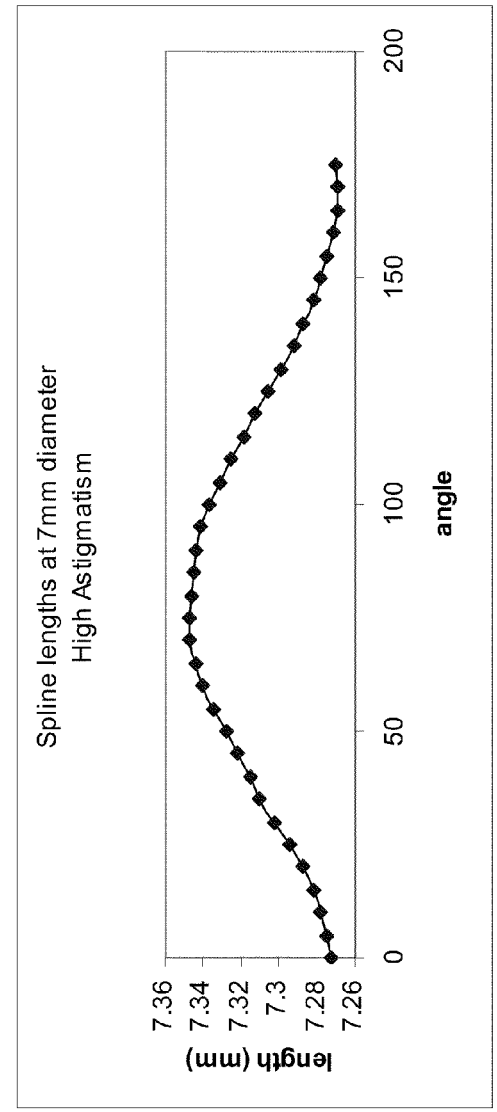
Fig. 15

Fig. 16
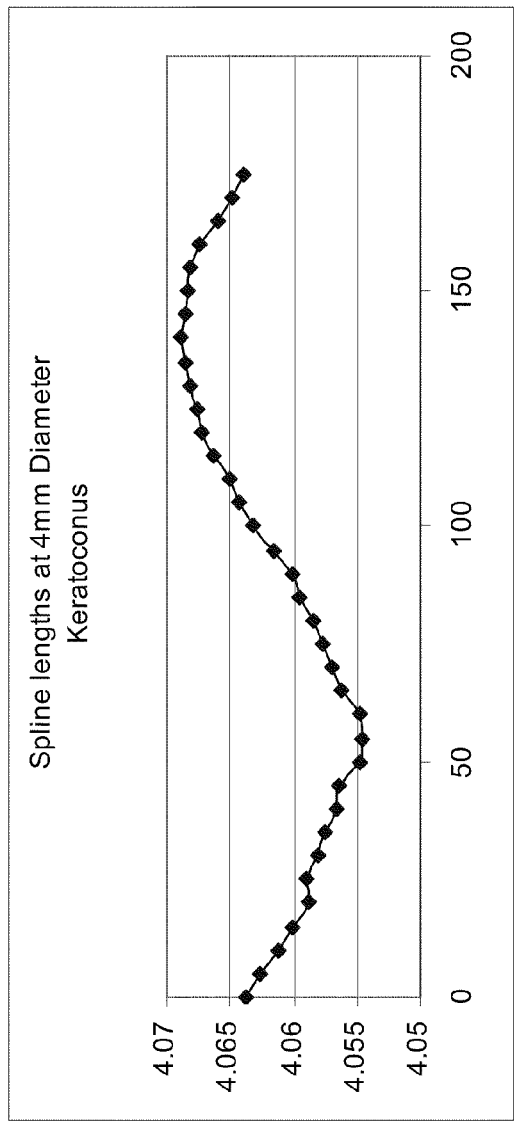
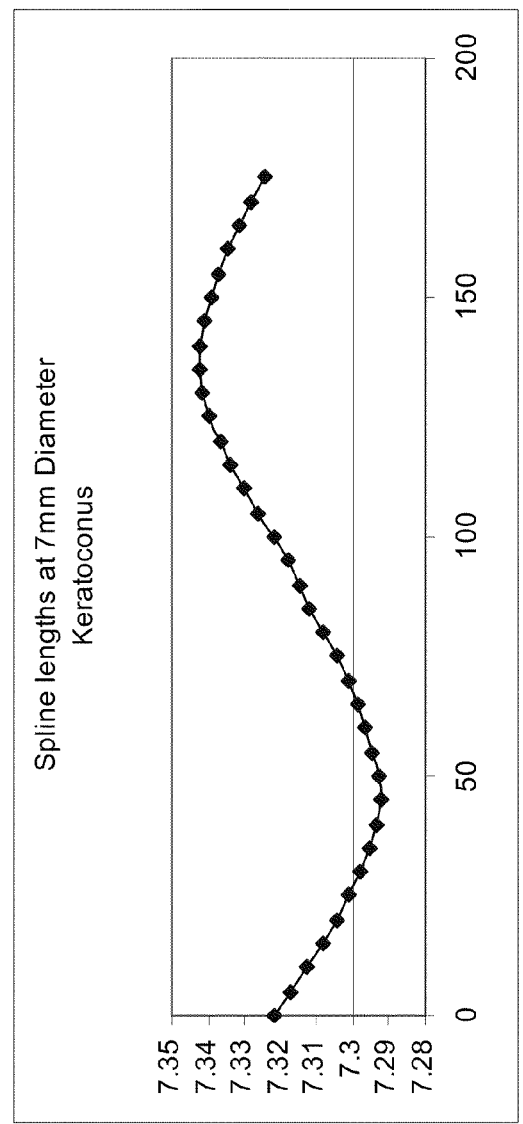

9 Year Change of Spline Length

Surface Area Change In 9 Years Of 0.04sq. mm. At 8mm Diameter

9 Year Change Of Spline Length

Fig.21 Keratoconus Eye

Advanced Keratoconus

Crescent Shape Has Evolved

Customary Elevation Display

Modified Elevation Model

"Happy Post LASIK"

"Miserable Post LASIK" Can't Read Yet Uncorrected 20/20

Relatively Decentered

Poor Reader Age 10: Labeled Dyslexic -1.00S and 20/20

Astigmatism Pentacam 1238
Anterior Surface
Rotationally Symmetric

Elevation Model at 8mm Diameter
Best-Fit Sphere = 7.202mm (46.86 Diopters)

Absolute Variance In The Rate Of Curvature Change    0.060718
Natural Variance In The Rate Of Curvature Change     0.09987
Average Rate of Curvature Change over all meridians  0.10625

Absolute Variance In The Rate Of Curvature Change    0.072536
Natural Variance In The Rate Of Curvature Change     0.072536
Average Rate of Curvature Change over all meridians  0.041161

Absolute Variance In The Rate Of Curvature Change    0.658738
Natural Variance In The Rate Of Curvature Change    0.658738
Average Rate of Curvature Change over all meridians    0.445276

Absolute Variance In The Rate Of Curvature Change    0.435502
Natural Variance In The Rate Of Curvature Change    0.435502
Average Rate of Curvature Change over all meridians    0.30547

Absolute Variance In The Rate Of Curvature Change   0.270327
Natural Variance In The Rate Of Curvature Change    0.675765
Average Rate of Curvature Change over all meridians 0.273655

DIAGNOSIS AND TREATMENT OF DISORDERS OF THE EYE

The present patent application is the U.S. national stage of International Application No. PCT/US07/21045, which was published in English on Apr. 10, 2008 and re-published in English on Oct. 9, 2008 under Publication No. WO 2008/042314. The International application and the present application claim the benefit of the filing date of the following U.S. provisional applications: No. 60/827,344, filed Sep. 28, 2006; No. 60/862,073, filed Oct. 19, 2006; No. 60/885,504, filed Jan. 18, 2007; and No. 60/913,557, filed Apr. 24, 2007. The disclosures of the International Application and the four provisional applications are hereby incorporated by reference in their entireties.

TECHNICAL FIELD

The present invention relates generally to the diagnosis and treatment of the eye and, more particularly concerns a method and system making use of a computerized model to diagnosis and monitor the condition of the eye.

BACKGROUND OF THE INVENTION

In our own U.S. Pat. No. 6,599,285, owned by the assignee of the present patent application, we disclosed a method for creating a computerized model which closely represents the surface of the cornea in three dimensions. A file representing sampled points in a corneal topography map of the surface of the cornea, for example the type produced by a corneal topography scanning machine, is read into a computer system running at a topological modeling computer program. The computer program then produces a surface model, which is displayed on the display of the computer system. Making use of the computer program, it is possible to simulate manipulations and operations upon the cornea. The model was used to simulate corneal ablation surgery on a patient's eye and to display the effect that the surgery would have on the eye. Using this approach, it was possible to demonstrate that a conventional intended operation would produce an irregular and undesirable surface. The model also made it possible to demonstrate that alternate approaches would have a better result. It was also possible to identify those patients that would not be good candidates for corneal ablation surgery. The same model was also used to determine the appropriate shape for a corrective contact lens with the pass-through surface that would conform closely to the surface of the cornea.

Making use of the computerized modeling techniques, we where able to demonstrate in our own U.S. Pat. Nos. 6,416, 179 and 6,669,342 also owned by the assignee of the present patent application) that ablation surgery could be performed or corrective contact lenses could be shaped so as to respect the natural shape of the cornea, while still providing the necessary vision correction. This was accomplished by estimating the surface model with a plurality of best fit half-meridian characteristic arcs which originate from a central point on the corneal model and extend to its periphery, each arc being rotationally spaced from its neighbor. Minimal adjustments could then be made to the curvature of each arc to achieve a modified corneal shape (a modified model) required for vision correction. This permits ablation surgery with minimal material removal and the contact lens which fits extremely closely to the cornea.

Making use of surface modeling, we discovered that the points of focus of different areas of the typical cornea are so dispersed that the cornea exhibits a substantial amount of axial and radial focus scatter. In our published US Patent Application No. 2006/0189966, owned by the assignee of the present patent application, we disclosed a technique for manipulating the surface model so as to shift the points of focus of different areas towards a predefined axis, to produce a modified surface model. The surface of the cornea or contact lenses can then be the conformed to the modified surface model, substantially reducing focus scatter. This typically improves the quality of vision for corneal ablation patients and contact lens wearers. In this patent application, we also disclosed the concept of analyzing the cornea by plotting parameters at the different characteristic arcs, for example, a plot of the curvature of each of the arcs as a function of its angular displacement.

The disclosures of U.S. Pat. No. 6,599,285; U.S. Pat. No. 6,416,179; U.S. Pat. No. 6,669,342; and published US Patent Application No. 2006/0189966 are hereby incorporated by reference in their entireties.

Despite all of the benefits obtained from using surface modeling, we had still not realized its full potential as a diagnostic tool.

Keratoconus is a disorder of the eye in which the cornea develops a conical shape which becomes more pronounced as the condition progresses. Early detection of the disorder is desirable, not only to ensure treatment, but to avoid procedures, such as refractive surgery, which should not be undertaken for patients with this condition. For example, patients with keratoconus are prone to corneal ecstasia following LASIK surgery. Corneal ecstasia is a dangerous condition in which the cornea exhibits central bulging and structural failure. Accordingly, it would be desirable to be able to detect easily the earliest presence of keratoconus.

SUMMARY OF THE INVENTION

We have since discovered that the surface model of the cornea or measurements taken from the model can be manipulated to reveal certain characteristics or "markers" that are indicative of the presence of disorders of the cornea, and certain disorders exhibit unique markers. Thus, through various manipulations of the characteristics of the surface model of a patient's cornea, we are able to reveal "markers" that are associated with disorders that are present in the eye.

In particular, we have discovered that the symptoms of keratoconus, can be detected first on the posterior surface of the cornea, and its reliable detection is possible at such an early stage as has never been possible before.

BRIEF DESCRIPTION OF THE DRAWINGS

The foregoing brief description and further objects, features and advantages of the present invention will be understood more completely from the following detailed description of presently preferred, but nonetheless illustrative, embodiments in accordance with the present invention, with a reference being had to the accompanying drawings, in which:

FIG. 15 illustrates a plot of spline length versus angular displacement at 4 mm and 7 mm diameters on the surface model for a highly astigmatic eye;

FIG. 16 contains similar plots to FIG. 15 but for a keratoconic eye;

DETAILED DESCRIPTION OF THE PREFERRED EMBODIMENTS

Figure 1:
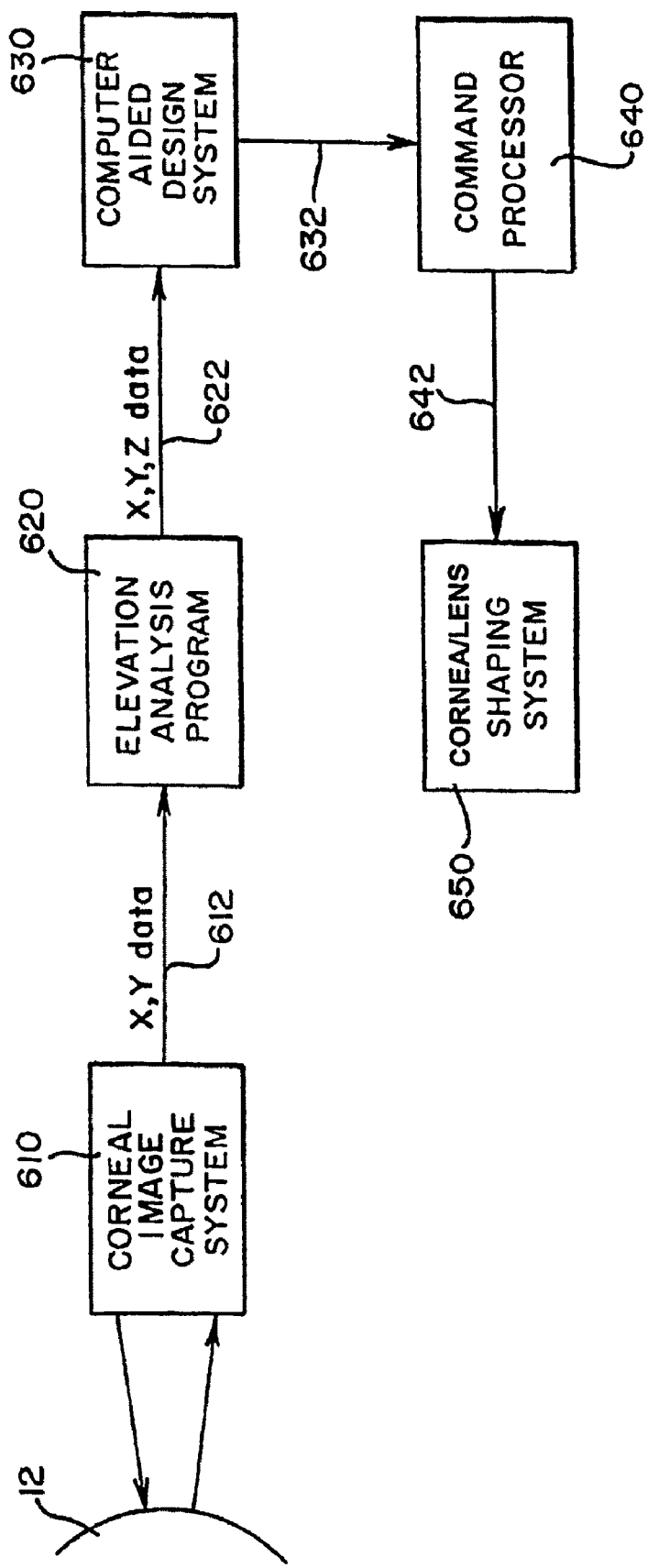
FIG. 1 is a block diagram illustrating a method for achieving vision correction in accordance with the present invention through either laser ablation of the cornea or an appropriately shaped contact lens.

A process for achieving laser ablation of the cornea and contact lens shaping making use of surface modeling is illustrated in block diagram form in FIG. 1. The process makes use of a Corneal Image Capture System 610, an Elevation Analysis Program 620, a Computer Aided Design System 630, a Command Processor 640 and a Cornea Shaping System 650. The Corneal Image Capture System 610, in conjunction with the Elevation Analysis Program 620, generates a three dimensional topographic map of the cornea of the patient. The Computer Aided Design System 630 is used as an aid in editing or modifying the corneal topographic data, to create a surface model, and data relating to the model is sent to a Cornea Shaping System 650 via the Command Processor 640. The Command Processor 640 uses the topographic data describing the surface of the cornea to be shaped from the Computer Aided Design System 630 to generate a sequence of commands/control signals required by the Cornea/Lens Shaping System 650. The Cornea/Lens Shaping System 650 accepts, from the Command Processor 640, a sequence of commands that describe the three dimensional movements of the Cornea/Lens Shaping System (any coordinate system may be used; e.g., Cartesian, radial or spherical coordinates) to shape the cornea or machine (e.g. a lathe) which is manufacturing a contact lens.

The Corneal Image Capturing System 610 and the Elevation Analysis Program 620 are preferably components of the PAR® Corneal Topography System ("the PAR® System"), which is available from PAR Vision Systems. The Elevation Analysis Program 620 is a software program executed by a processor, for example an IBM™ compatible PC. Program 620 generates a third dimension element (a Z coordinate representing distance away from a reference plane inside the eye) for each of a plurality of sample points on the surface of the cornea measured by system 610. Each point is defined by its X-Y coordinates as mapped into the reference plane, and its Z coordinate is determined from brightness of the point. One method of calculating the elevation of each point, i.e., the z-coordinate, is by comparing the X-Y and brightness values measured from the patient's cornea 14 with the coordinates and brightness of some reference surface with known elevation, e.g., a sphere of a known radius. The reference values can be pre-stored.

The final output of the Elevation Analysis Program 620 is the X-Y-Z coordinates for a multiplicity of sample points, known as a point cloud, on the surface of the cornea 14. It will be apparent to those skilled in the art that any method can be used that can generate X, Y, Z corneal data providing both location and elevation information for points on the corneal surface with the required accuracy. In the preferred embodiment about 1200 points are spaced in a grid pattern, as viewed in the X-Y plane, so the projections of the points into the X-Y plane are about 200 microns apart. The Pentacam system discussed below has a spacing of 100 microns and gives coverage out to at least 9 mm on the cornea.

The X-Y-Z data output from the Elevation Analysis Program 620 can be formatted in any number of well-known machine-specific formats. In the preferred embodiment, the data are formatted in Data Exchange File (DXF) format, an industry standard format which is typically used for the interapplication transfer of data. A DXF file is an ASCII data file, which can be read by most computer aided design systems.

Figure 2:
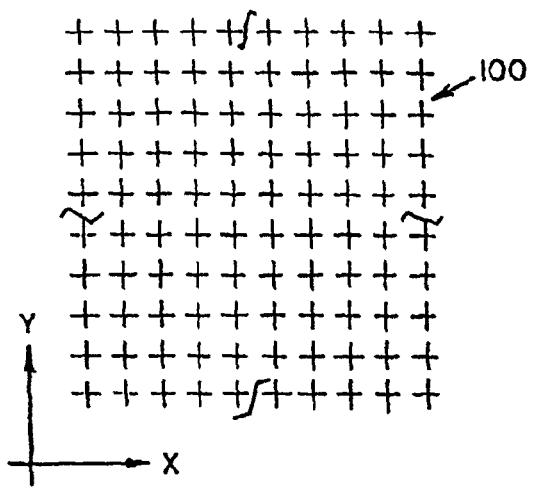
FIG. 2 is a schematic diagram illustrating a plan view of a point cloud as obtained with a corneal image capture system.
Figure 3:
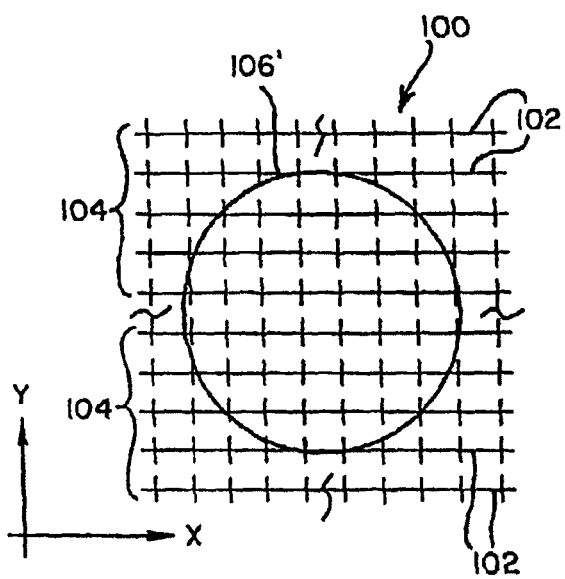
FIG. 3 is a schematic plan view similar to FIG. 2 illustrating a plurality of splines and how they are connected through the data points of the point cloud.
Figure 4:
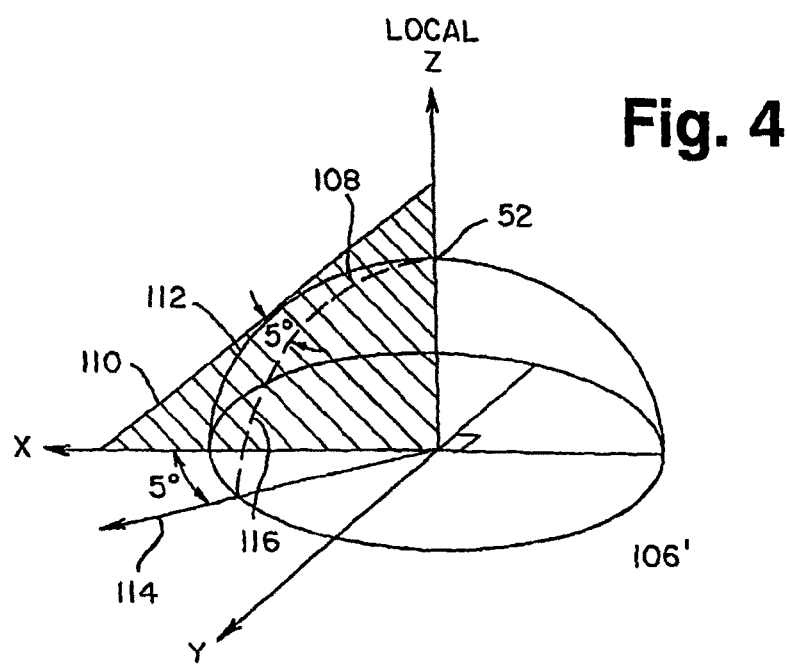
FIG. 4 is a perspective view of a cornea matching surface illustrating how characterizing curves are constructed.

Referring now to FIGS. 2 and 3, a point cloud 100 is depicted as it would appear when viewing the reference plane along the Z-axis (i.e., as projected into the X-Y plane). Each point corresponds to a particular location on the patient's cornea. The data are usually generated from an approximately 10 mm×10 mm bounded area of the cornea, the working area. Thus, there may be as many as 50 rows of data points. A surface 108 (see FIG. 4) that models or matches the topography of the surface of the patient's cornea is generated by the computer aided design system 630 from the data points generated by the Elevation Analysis Program. In a preferred embodiment, Computer Aided Design System 630 is the Anvil5000™ program which is available from Manufacturing Consulting Services of Scottsdale, Ariz.

Cornea matching surface 108 is preferably produced by first generating a plurality of splines 102, each defined by a plurality of the data points of the point cloud 100. The generation of a spline that intersects a plurality of data points (i.e., knot points) is, per se, known to those skilled in the art and can be accomplished by the Anvil5000™ program once the input data have been entered. For more information regarding the generation of a surface model, see U.S. Pat. No. 5,807,381, the disclosure of which is incorporated herein by reference. In a preferred embodiment, the known nonuniform rational B-spline formula is used to generate the splines, but they could be generated by other well-known mathematical formulas for splines, such as the cubic spline formula or the rational uniform B-spline formula. As illustrated in FIG. 3, in a preferred embodiment, each of the splines 102 lies in a plane that is parallel to the X and Z axes and includes a row of points from the cloud 100 in FIG. 3.

Surface 108, which matches the corneal surface of the scanned eye, is then generated from splines 102. There are a number of well-known mathematical formulas that may be used to generate a surface from a plurality of splines 102. In the preferred embodiment, the well known nurb surface equation is used to generate a corneal surface from splines 102. In the embodiment, because the useful scanned area of the eye is approximately 8 mm×8 mm, approximately 50 splines 102 are created. As illustrated in FIG. 3, a skinned surface segment 104 is created for a small number (e.g., five) of the adjacent splines. Adjacent skinned surface segments 104 share a common border spline. Thus, about ten skinned surface segments are generated from the point cloud and are then merged together by the Anvil 5000™ program in a manner known to those skilled in the art, to produce one composite surface 108.

Neither the original data points, nor the knot points of splines 102 necessarily lie on surface 108, owing to the mathematical generation of the surface when using the nurb surface equation formula. However, the surface 108 estimates those points within a predefined tolerance.

The HIGH point on the generated corneal matching surface 108 (i.e., the point having the greatest Z value) is determined. A cylinder 106 of a predetermined diameter is then projected onto the corneal matching surface 108 along an axis which is parallel to the Z-axis and passes through the HIGH point. Cylinder 106 preferably has a diameter of 4 mm-7 mm, typically 6 mm, and the closed contour formed by the intersection of cylinder 106 with surface 108 projects as a circle 106' in the X-Y plane. On the matching surface 108, this contour defines the outer margin 26 of the working area of the cornea. The cornea is the most symmetric and spherical about the HIGH point and, therefore, provides the best optics at this point.

The outer margin 26 must fit within the point cloud, so that the surfaces of the cornea can be formed based on the measured corneal data. The computer aided design system 630 can then illustrate a default circle 106' (in the X-Y plane) with respect to the point cloud, for example on a monitor screen, so that the operator can be assured that circle 106' falls within the point cloud. Additionally, system 630 can be set up to determine if circle 106' falls within point cloud 100 and, if it does not fall completely within point cloud 100, to alert the user to manipulate the circle (i.e., move the center point and/or change the radius of the circle) so that circle 106' lies within the corneal data point cloud 100. In a worst case scenario, the eye should be rescanned if insufficient data is available from the scanned eye to ensure that the working area of the cornea will fit properly within the point cloud. Alternatively, the area of the point cloud can be made larger.

It is to be understood that circle 106' is only a circle when viewed in the X-Y plane (i.e., looking along the Z-axis). Actually, the periphery 26 is approximately elliptical and lies in a plane which is tilted relative to the reference plane. A line perpendicular to this tilted plane which passes through the HIGH point will be referred to as the "LOCAL Z-AXIS" or "tilted axis", and the tilt of the tilted plane relative to the reference plane will be considered the tilt angle of the working area of the cornea.

The central cornea is, on average, about 450 µm thick centrally. In most corneal ablation procedures, which involve about 3 diopters of attempted correction on average, less than 100 µm depth of cornea is ablated, because there is virtually no risk of scarring with the type of lasers that are typically used. Most refractive surgeons are not concerned re as to how much is removed from the anterior cornea. Their concern is what is left after the ablation. 250 microns is now considered the "safe" limit. Beyond the 100 µm depth, the risk of scarring increases. For example, a 120 µm depth ablation is known to cause scarring. However, there exists the possibility that the risk of scarring for deeper ablations may be reduced by drug therapy prior to or contemporaneous with the laser treatment. The magnitude of the corneal undulations is typically about fifteen to twenty microns from the crest of a hill to the trough of a valley and may be as great as about thirty microns.

The surgical procedures performed in accordance with the present invention and optical lenses manufactured in accordance with the invention will seek to correct the patient's vision in accordance with the required corrections established in a "refraction test." When this test is performed, the patient sits in chair which is fitted with a special device called a "phoropter", through which the patient looks at an eye chart approximately 20 feet away. As the patient looks into the phoropter, the doctor manipulates lenses of different strengths into view and, each time, asks the patient whether the chart appears more or less clear with the particular lenses in place. In practice, the doctor is able to vary the power or diopter correction about two orthogonal axes, as well as the degree of rotation of those axes about a Z-axis along the line-of-sight. The doctor continues to modify these three parameters until he achieves the optimum vision. The results of the refraction test are usually given in the form "a, b, c°", where "a" is the diopter correction at the first axis, "b" is the additional diopter correction required at the second, orthogonal axis, and "c°" is the angle of rotation of the first axis relative to the horizontal. This angle of rotation is associated with astigmatism. The indicated form of result information is given for each eye and is immediately useful in grinding a pair of lenses for eyeglasses.

For the purposes of the present invention, it is preferred to perform a modified form of refraction test. For this modified form of refraction test, the doctor adjusts the phoropter at a series of equally spaced angles, say every 15° from the horizontal, and obtains the optimum refraction at each angle. Typically, the more angles that are measured, the better the results. However, since the refraction measurements can be time consuming, 15° increments, which result in a total of 12 readings, seem to be a reasonable number. The manner of using the modified refraction test will be described in detail below.

There will now be described a technique for generating characterizing curves on surface 108, which will be useful below. A plane 110 is constructed which contains the LOCAL Z-AXIS (See FIG. 4). The intersection between plane 110 and surface 108 defines a first characterizing curve 112. Plane 110 is then rotated about the LOCAL Z-AXIS, for example by a 5° increment counterclockwise, as represented by line 114, where its intersection with surface 108 defines a second characterizing curve 116, which is illustrated as a dashed line in FIG. 4. This process continues at fixed rotational increments about the LOCAL Z-AXIS, for example every 5°, until plane 110 has swept 360°, to produce a complete set of characterizing curves (meridians), in this case seventy-two (360°/5).

Each of these characterizing curves is then estimated by a best-fit spherical (circular) arc. One manner of doing this is simply to select a circular arc which passes through three known points for each curve (e.g. the point at which it touches the contour 106', the HIGH point, and that point which is halfway between those two points when viewed in projection along the local Z axis). Once the spherical arcs are generated, the focal point of a portion of the cornea represented by a circular arc can be estimated by the center of that arc. Techniques for locating the center of a spherical arc are well-known.

Keratoconus is a disorder of the eye in which the cornea develops a conical shape which becomes more pronounced as the condition progresses. Early detection of the disorder is desirable, not only to ensure treatment, but to avoid procedures, such as refractive surgery, which should not be undertaken for patients with this condition. For example, patients with keratoconus are prone to corneal ecstasia following LASIK surgery. Corneal ecstasia is a dangerous condition in which the cornea exhibits central bulging and in some cases structural failure necessitating corneal transplant surgery. Accordingly, it would be desirable to be able to detect easily the presence of keratoconus.

Figure 5:
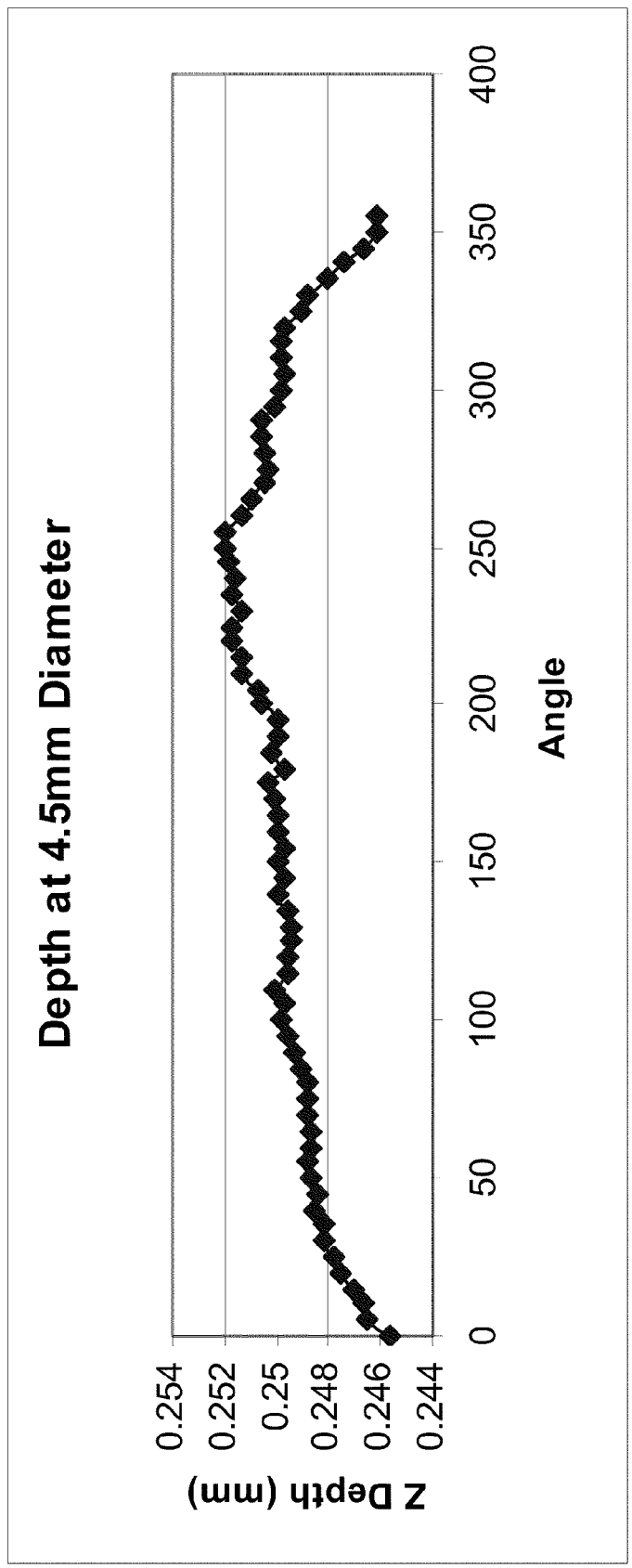
FIG. 5 is a plot of corneal depth at a diameter of 4.5 mm for an eye with excellent corrected vision (better than 20/20 with no refractive astigmatism)

It has been found that an analysis of corneal depth as a function of radial displacement on the surface of the cornea can provide an indication or a "marker" for the presence of keratoconus. For example, although any diameter can be used for plotting, FIG. 5 is a plot of corneal depth at a diameter (about the HIGH point—all diameters will hereafter be assumed to be about the High point unless stated otherwise) of 8 mm for an eye with excellent corrected vision (better than 20/20 without refractive astigmatism). It should be noted that the resulting curve is gentle, smooth, and continuous with a depth variation of only 6 μm. The maximum depth occurs at an angle of approximately 270°, where the rotational angle is defined as 0° at the nose, and rotation is so that 90° is in the upper part of the eye and 270° is in the lower. Since this models an actual corneal surface, it will be appreciated that there will typically be variation from one eye to another. It is also possible to have a slight sinusoidal shape to the curve, but this amount of variation is typical. The variation can be expected to be smaller for an eye with better acuity and larger for one with lesser acuity. For example, for an eye with 20/25 corrected vision, the variation might be 25 μm.

Figure 6:
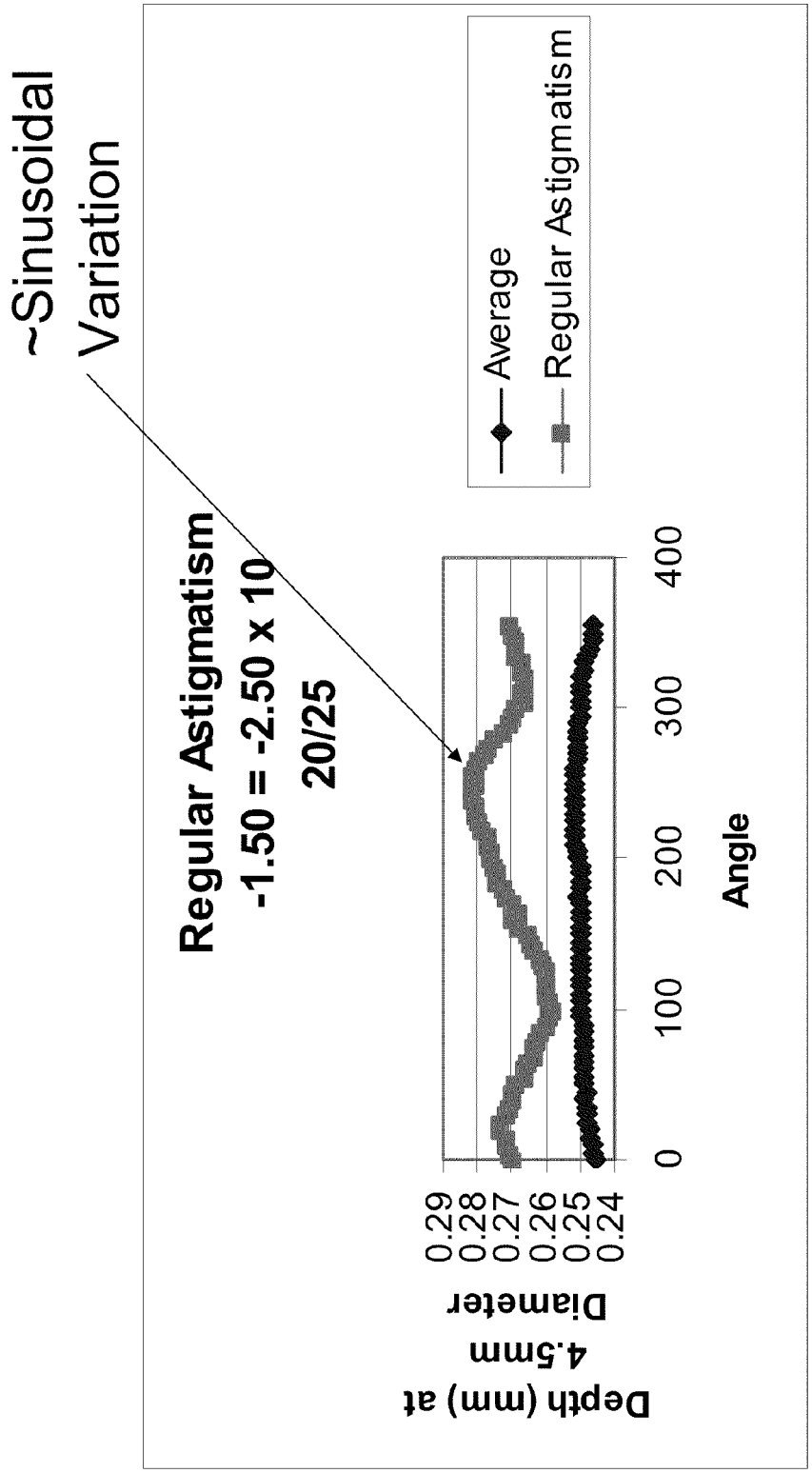
FIG. 6 is a plot similar to FIG. 5, but for an eye having 1.5 diopters of regular astigmatism and Snellen visual acuity of 20/25.
Figure 7:
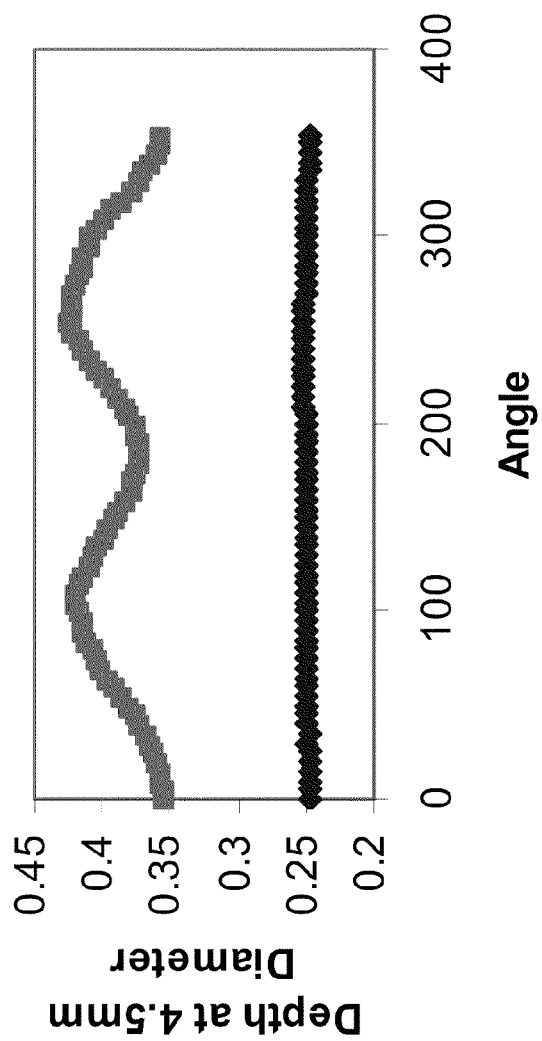
FIG. 7 illustrates a plot similar to FIG. 6, but in this case, the eye has a relatively high regular astigmatism of about 6 diopters and corrected acuity.

FIG. 6 is a plot similar to FIG. 5, but for an eye having 1.5 diopters of regular astigmatism and Snellen acuity of 20/25. In this case, the depth of the cornea exhibits a pronounced sinusoidal shape that has the same depth variation as an eye with similar acuity and without astigmatism, and it has an average value which is approximately 20 μm above that of an average eye. This is also approximately the same as for an eye of similar acuity and no astigmatism. FIG. 7 illustrates a plot similar to FIG. 6, but in this case, the eye has a relatively high regular astigmatism of about 6 diopters. In this case, the eye exhibits about 60 μm of depth variation, with an average depth that is approximately 125 μm more than an average eye.

Figure 8:
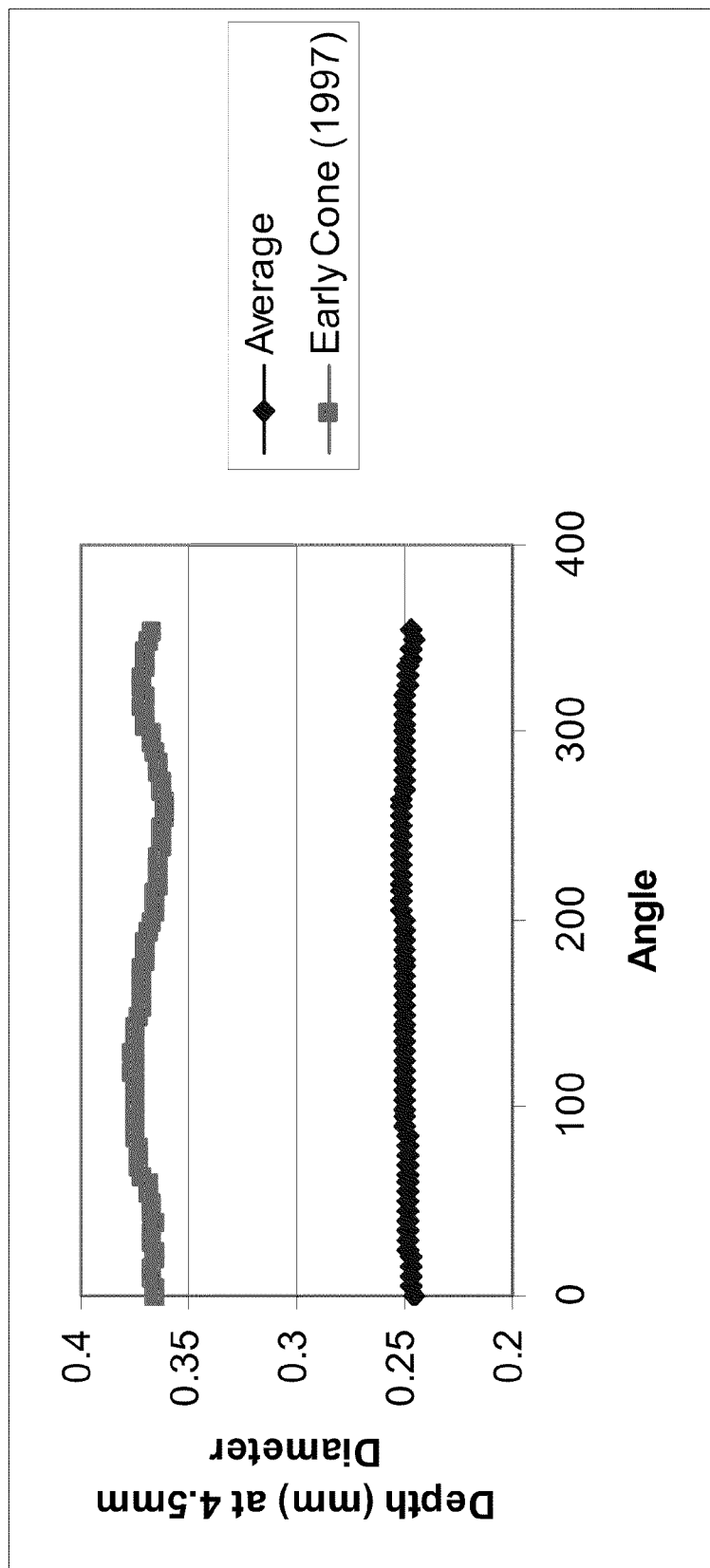
FIG. 8 is a plot similar to FIG. 5 for an eye exhibiting early keratoconus.

FIG. 8 is a plot similar to FIG. 5 for an eye exhibiting early keratoconus. In this case, a very small, essentially negligible, sinusoidal variation of depth is present, and the average depth is slightly in excess of 100 μm, an order of magnitude more than an average eye.

Figure 9:
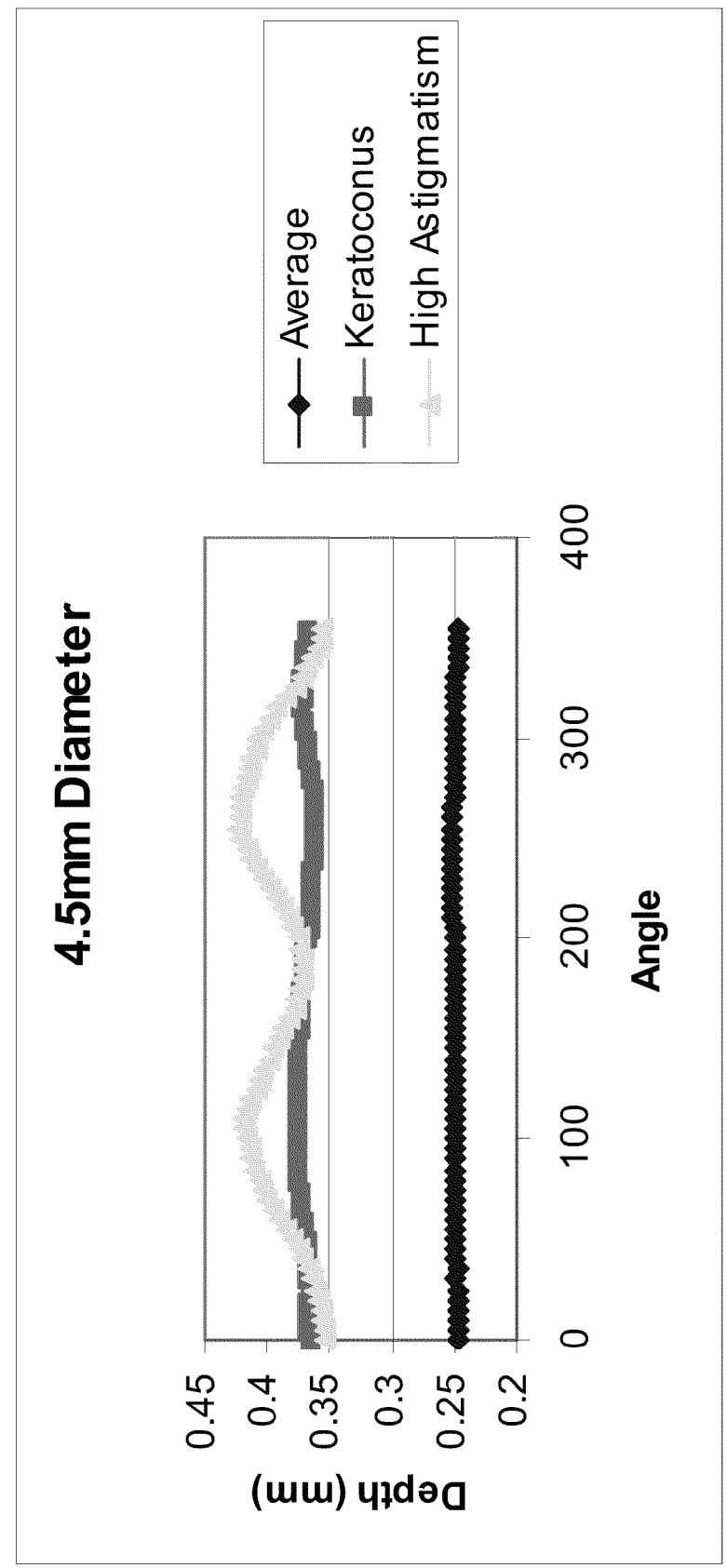
FIGS. 9 and 10 are similar plots showing corneal depth of an average eye, a keratoconic eye, and a highly astigmatic eye as a function of rotational position at 4.5 mm and 7 mm diameters of the cornea, respectively.
Figure 10:
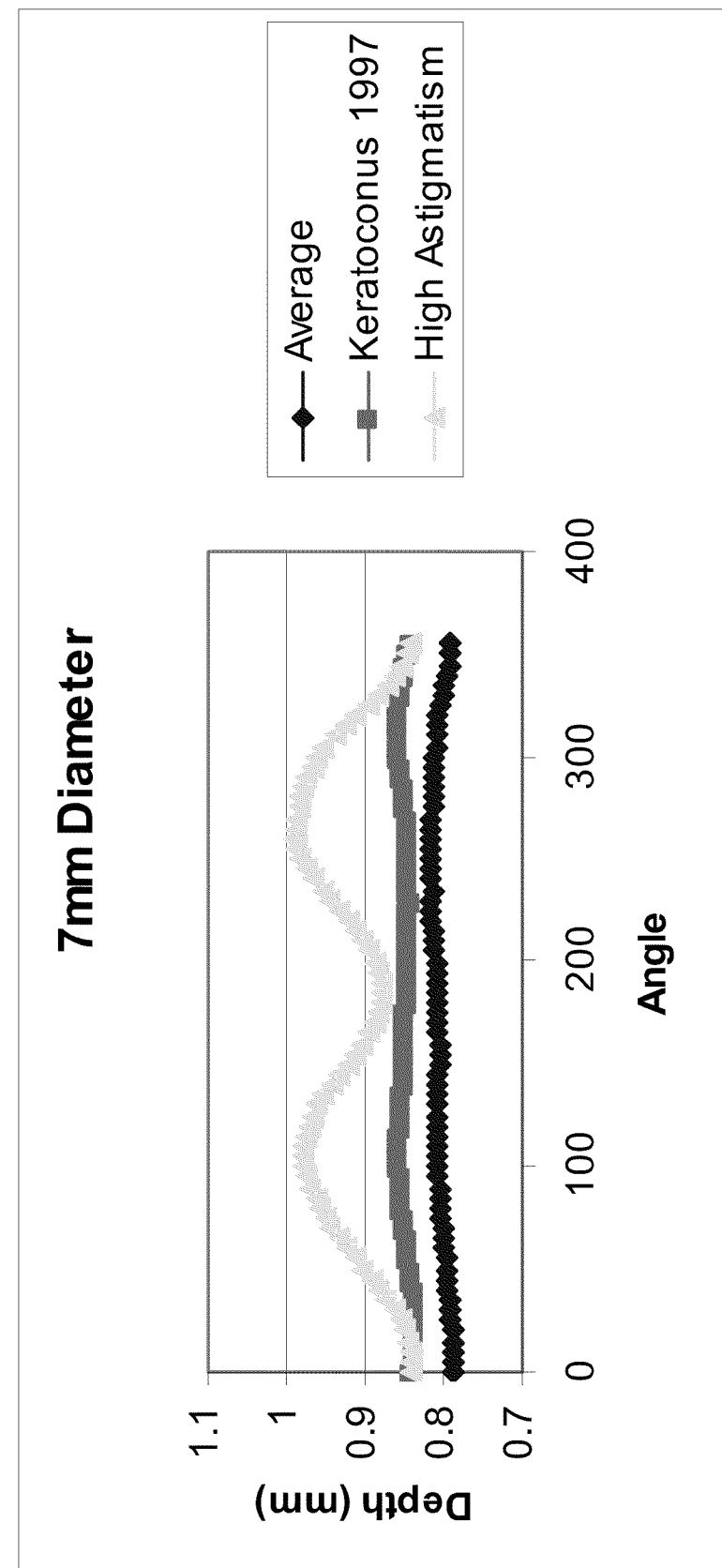

FIGS. 9 and 10 are similar plots showing corneal depth of an average eye, a keratoconic eye, and a highly astigmatic eye, as a function of rotational position, at 4.5 mm and 7 mm diameters of the cornea, respectively. At 4.5 mm, the average depths of the keratoconic and astigmatic eyes are approximately the same, 100 μm deeper than an average eye, that the astigmatic eye exhibits a substantial sinusoidal variation of about 50 μm. At 7 mm, the keratoconic eye is only about 50 μm deeper than an average eye, and the astigmatic eye remains 100 μm deeper and exhibits a sinusoidal variation which is about twice that at 4.5 mm. Thus, although it might be difficult to distinguish keratoconus from high astigmatism by observing the corneal depth variation centrally, if the corneal depth variation is also observed both centrally and peripherally, the two conditions can be distinguished.

Figure 11:
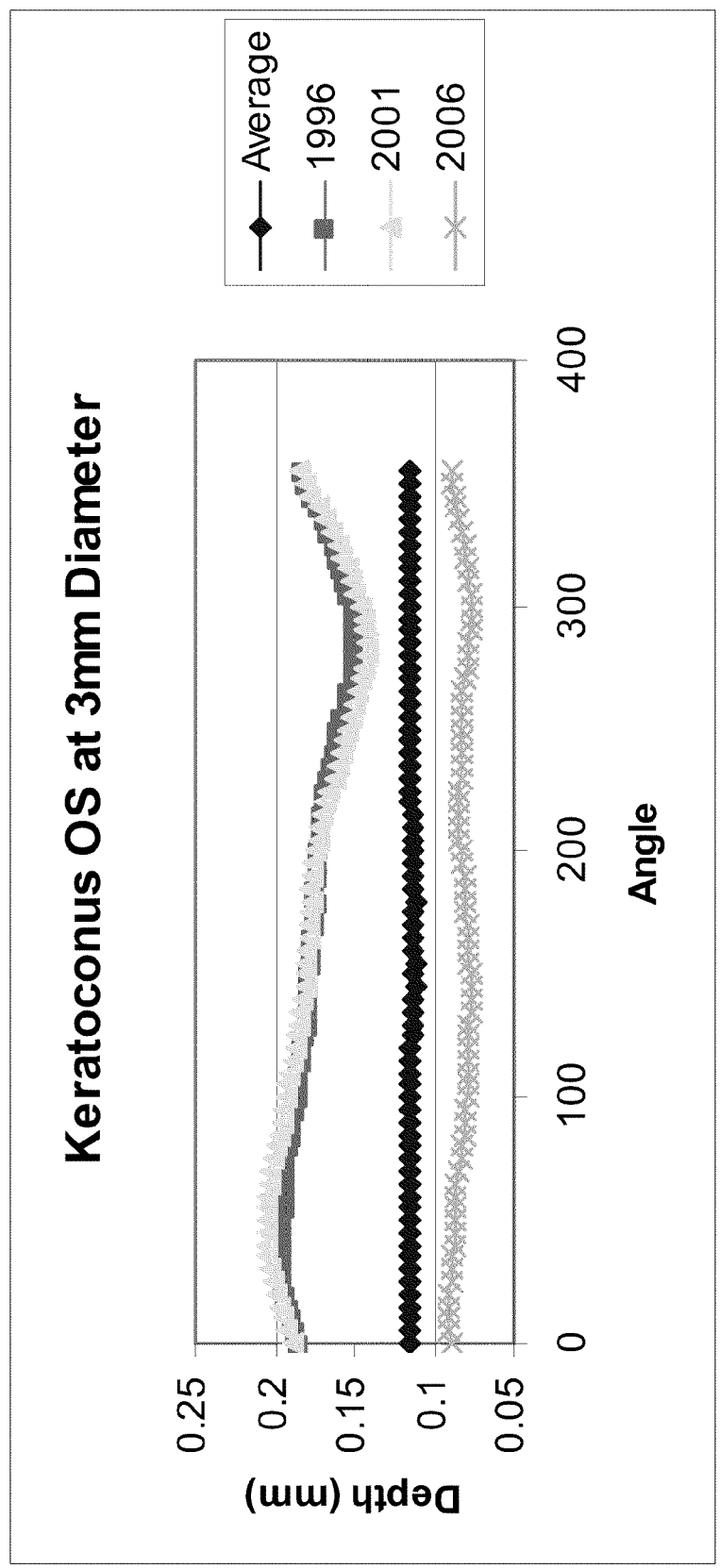
FIGS. 11-13 illustrate the angular variation of depth of the keratoconic cornea over time at diameters of 3 mm, 4.5 mm, and 7 mm, respectively.
Figure 12:
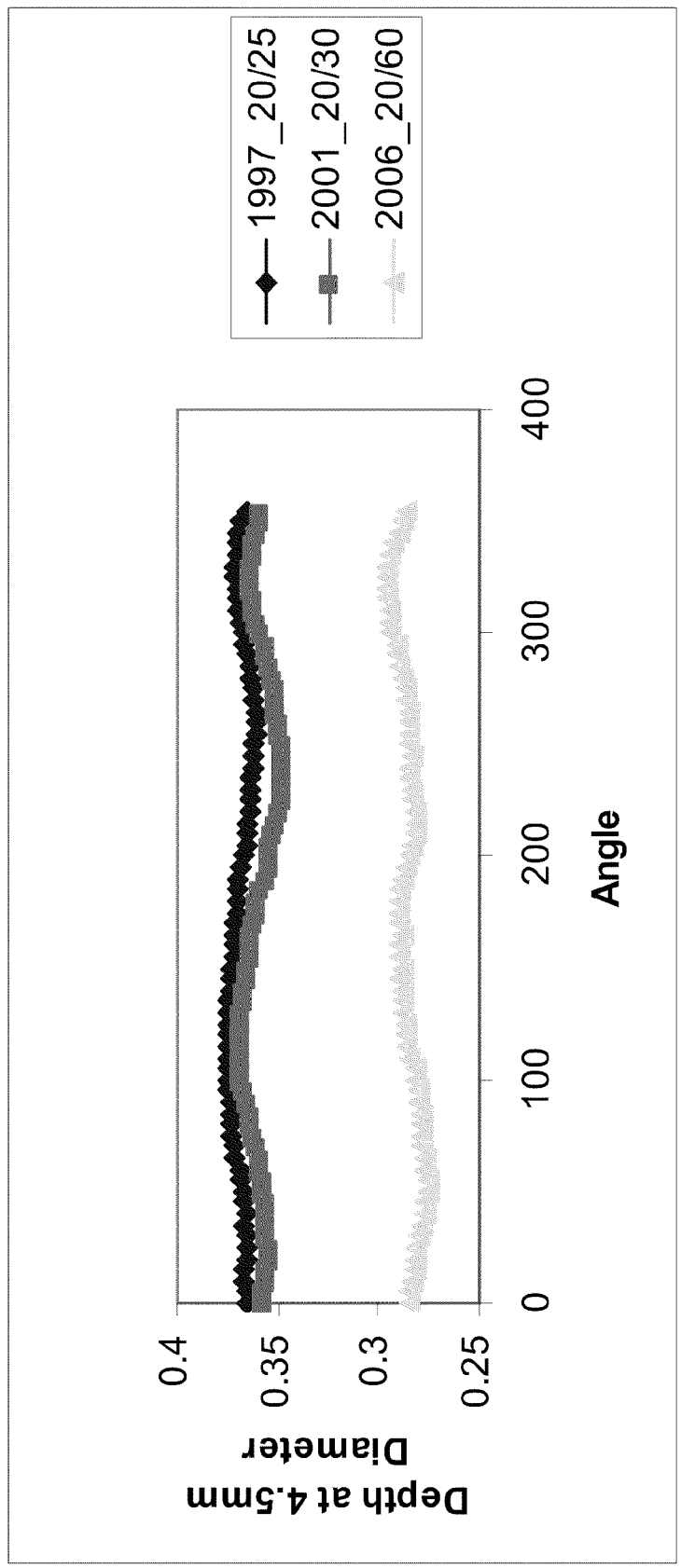
Figure 13:
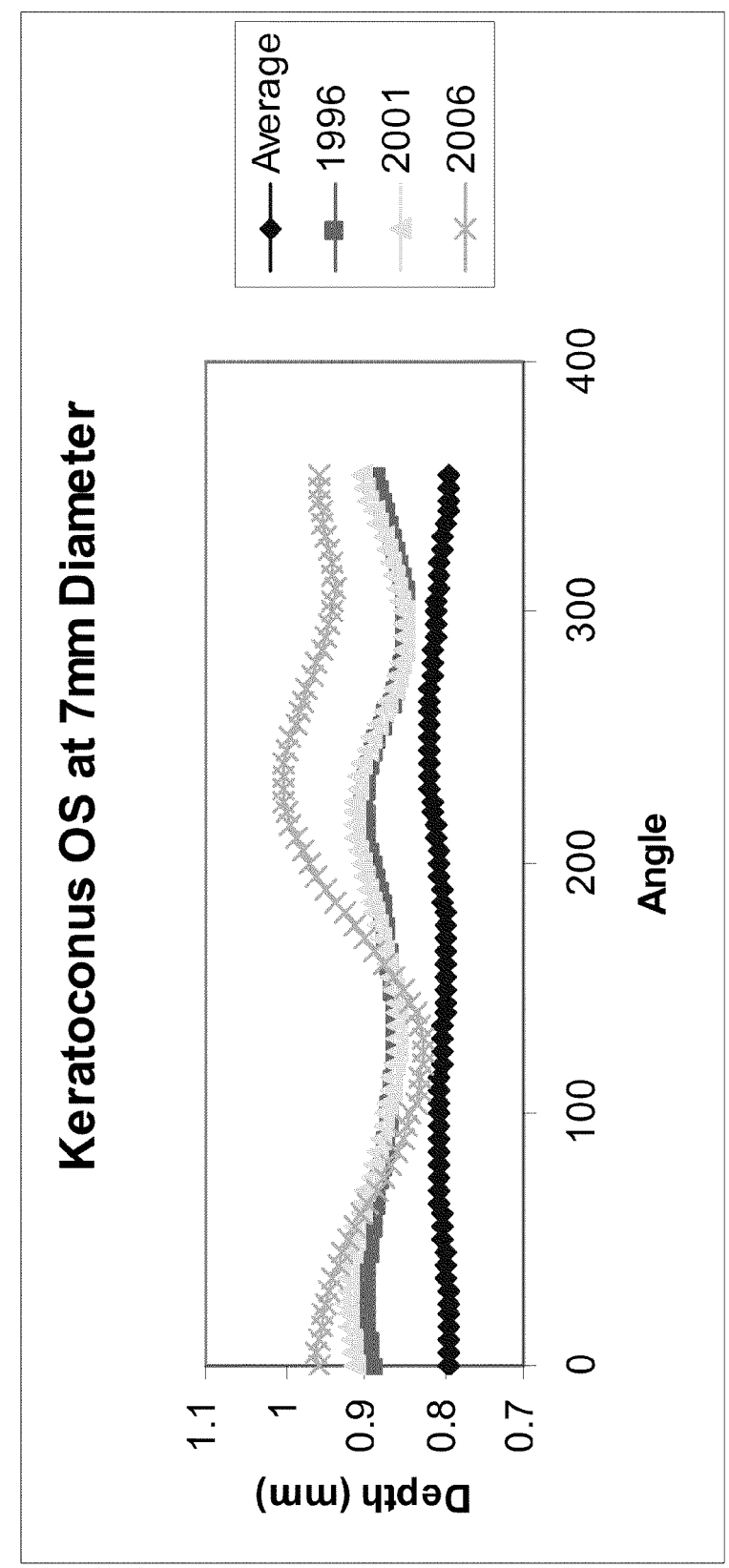

The present invention is also useful in analyzing the progression of the keratoconic eye over time. For this purpose we compare the depth of the cornea as a function of angular position at various diameters to its depth at the point of most symmetry (the HIGH point), over time. FIGS. 11-13 illustrate the angular variation of depth of the keratoconic cornea over time at diameters of 3 mm, 4.5 mm, and 7 mm, respectively. It is noteworthy that, while the peripheral cornea of the keratoconic eye gets deeper overtime, the central portion of the cornea becomes shallower.

Figure 14:
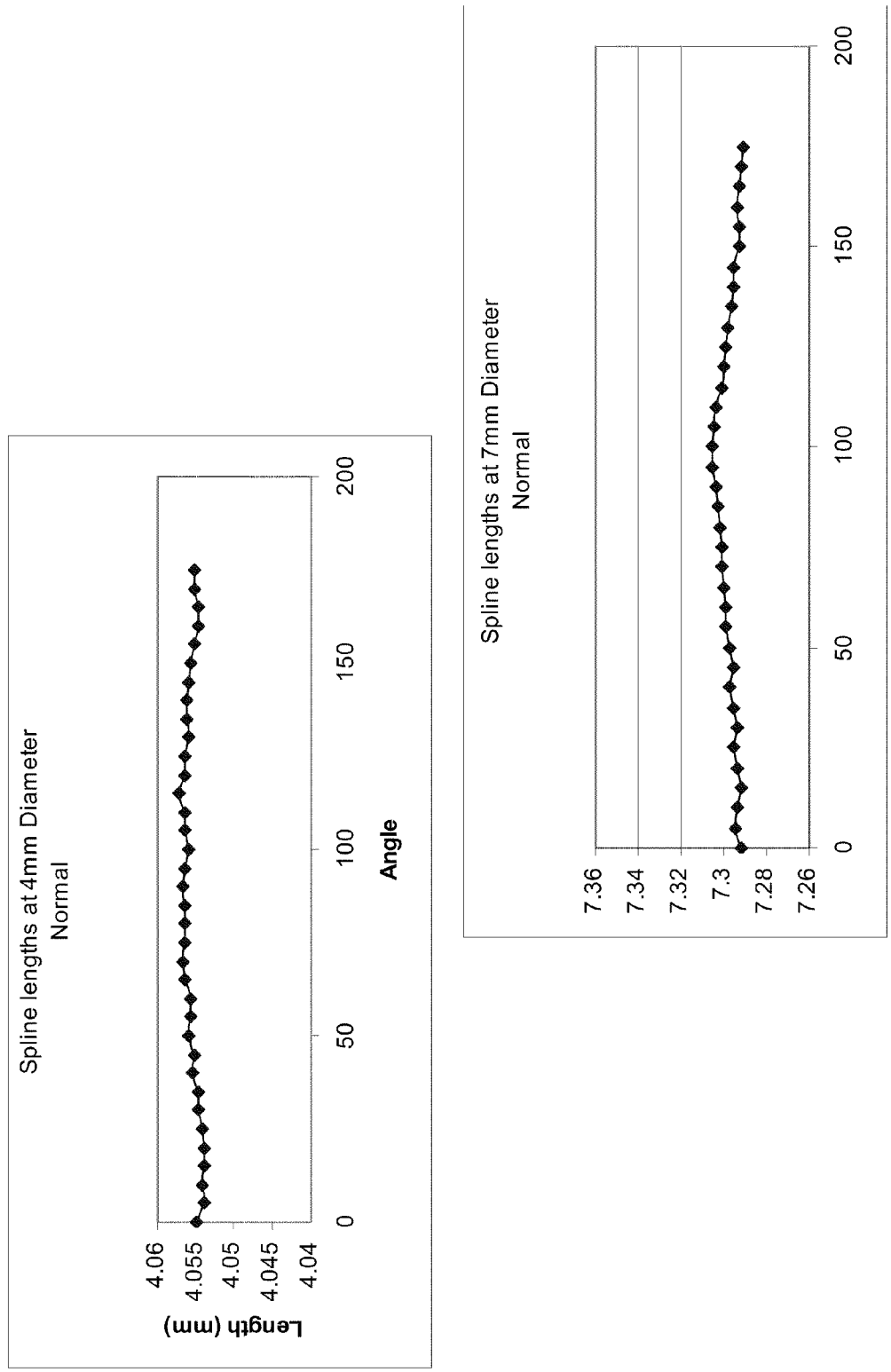
FIG. 14 is a plot, for a normal eye, of spline length as a function of the angular orientation of the spline at 4 mm and 7 mm diameters on the surface model.

Another way to monitor disorders of the eye is to measure the length of each spline or meridian on the surface model which passes through the HIGH point. FIG. 14 is a plot, for a normal eye, of spline length as a function of the angular orientation of the spline at both 4 mm and 7 mm diameters on the surface model. For all intents and purposes, the spline lengths can be considered to be constant. FIG. 15 illustrates a plot of spline length versus angular displacement at 4 mm and 7 mm diameters on the surface model for an eye with high astigmatism, and FIG. 16 contains similar plots for a keratoconic eye. It should be noted that in FIG. 15, both curves are approximately cosinusoidal with a period corresponding to a half rotation of the surface model, and in FIG. 16, both curves are approximately sinusoidal, with a period corresponding to a half rotation of the surface model. Accordingly, the "markers" for a highly astigmatic eye and a keratoconic eye are very distinguishable. Therefore, the capability of detecting a highly astigmatic eye and a keratoconic eye could be greatly improved by studying plots of both corneal depth and spline length for a particular patient.

Figure 17:
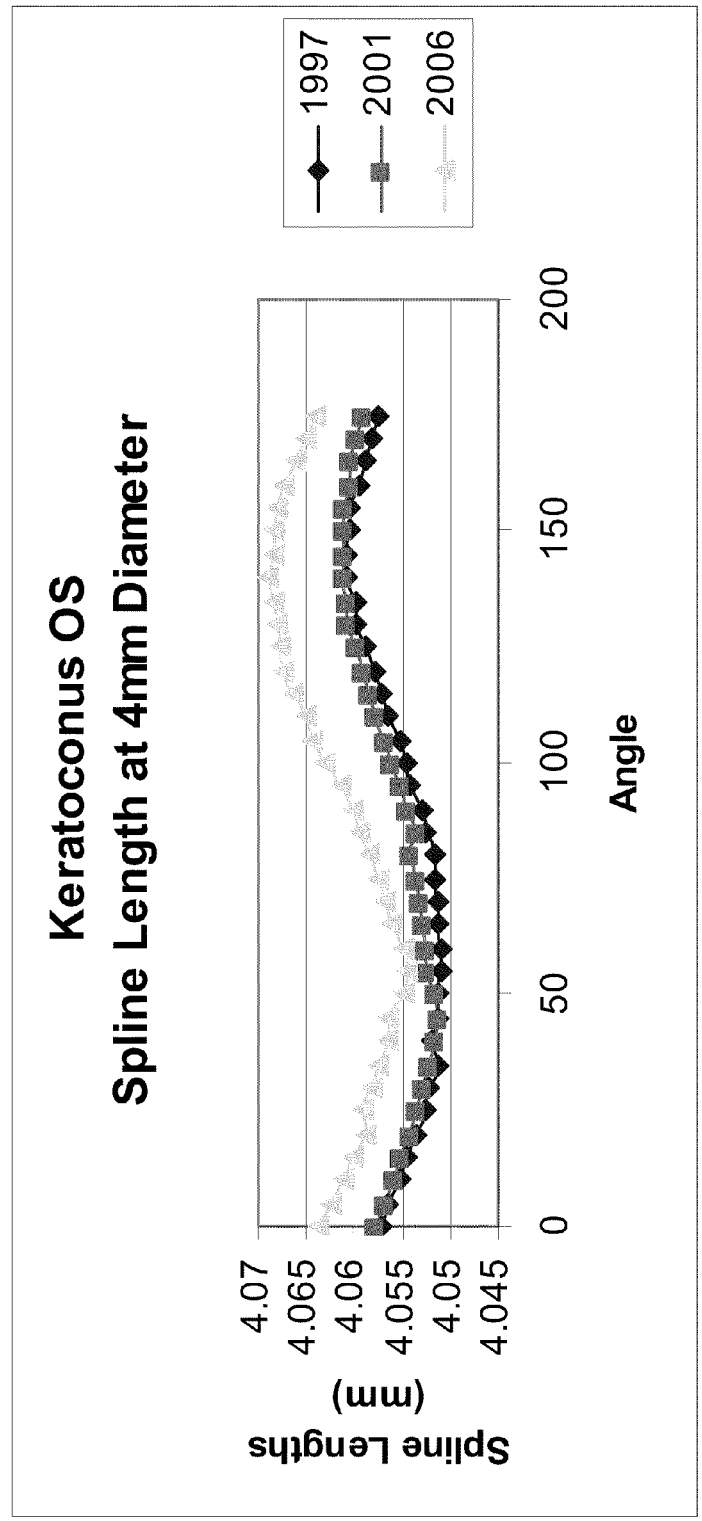
FIGS. 17 and 18 are plots of spline length as a function of angular orientation at 4 mm and 7 mm diameters, respectively, demonstrating the variation of spline a length over time.
Figure 18:
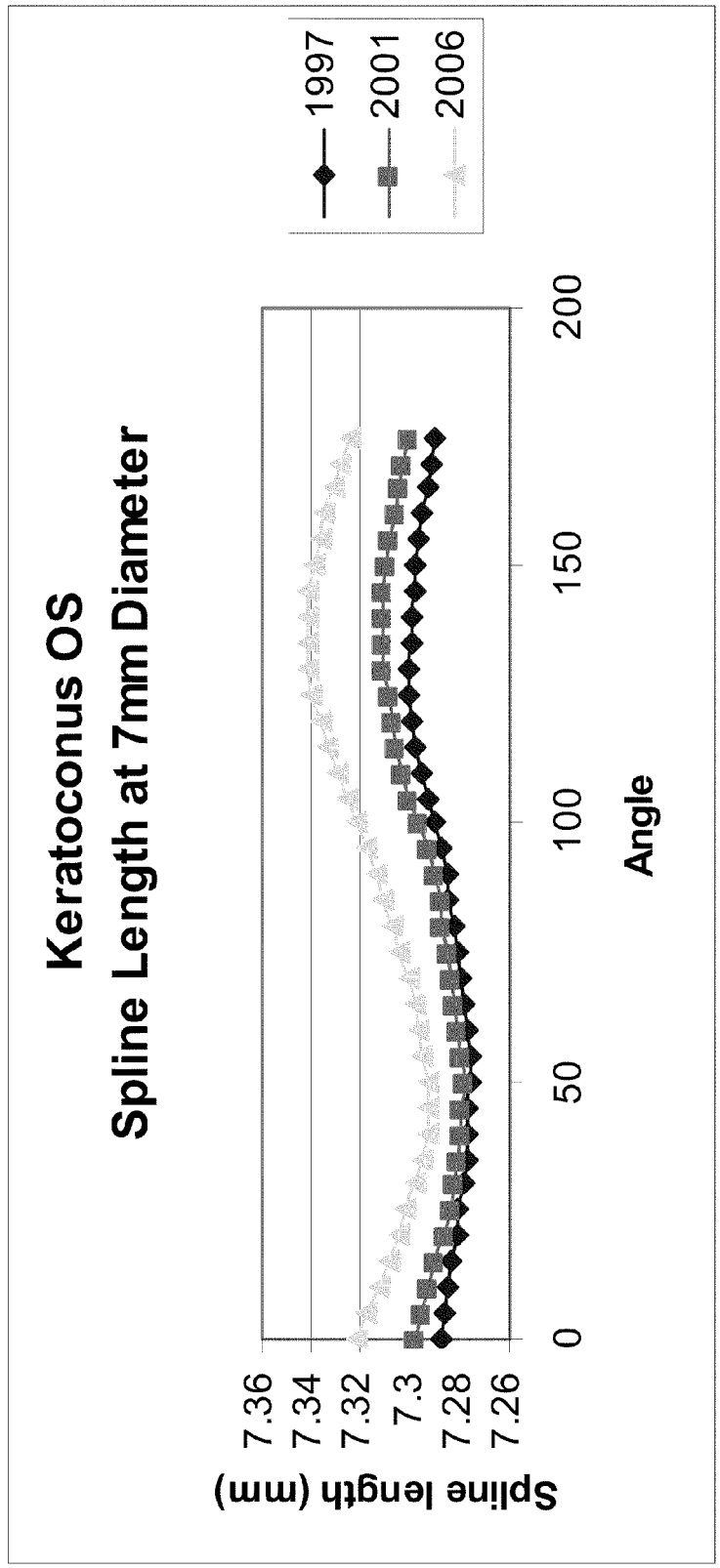

FIGS. 17 and 18 are plots of spline length for a keratoconic eye as a function of angular orientation at 4 mm and 7 mm diameters, respectively. These plots demonstrate the variation in spline length that occurs over time in a diseased eye thus providing a relatively quantitative description of the progression of keratoconus. As may be seen, spline length increases over time, both centrally and peripherally. Accordingly, this is another basis for distinguishing between an astigmatic eye and a developing keratoconic eye.

Figure 19:
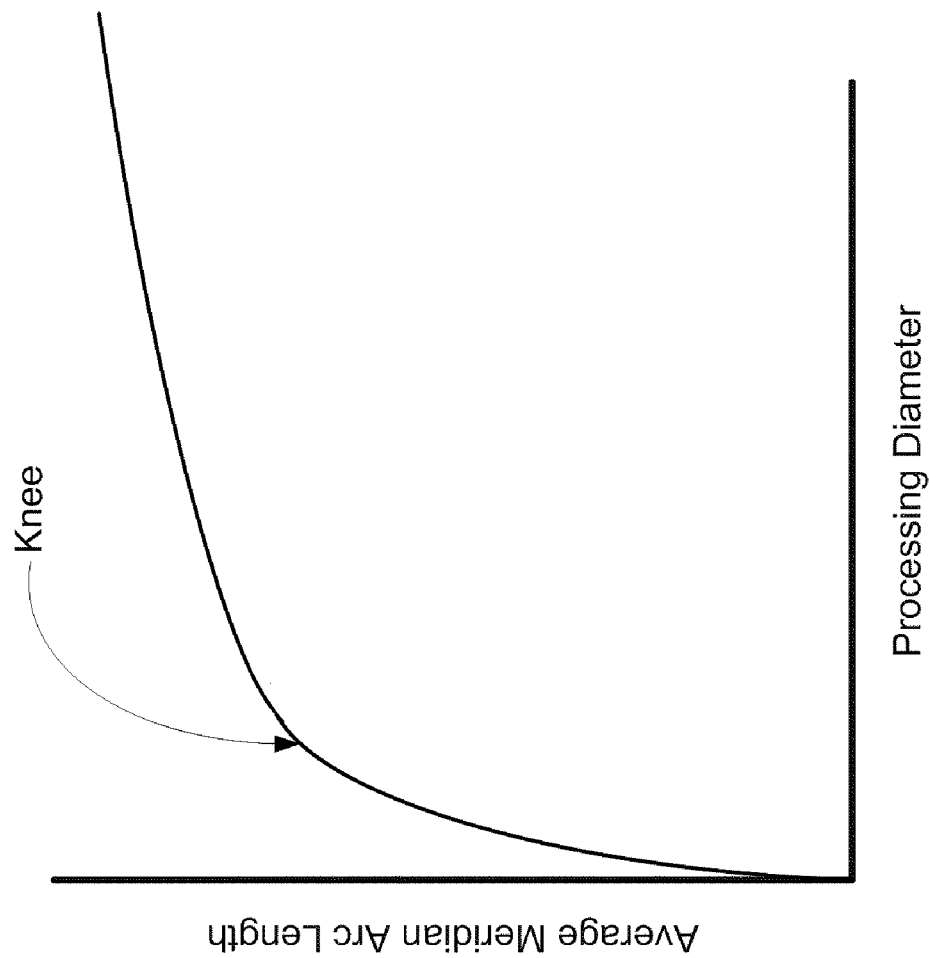
FIG. 19 illustrates a curve of the type that is generated with respect to the surface model in order to determine the best fit sphere to use for modified elevational displays in accordance with a further embodiment of the invention.

There will now be described yet another procedure for creating "markers" for identifying a keratoconic eye. Initially, a curve of the type illustrated in FIG. 19 is generated with respect to the surface model. This is done by selecting a processing diameter of the surface model and generating a plurality of characterizing arcs in the corresponding portion of the surface model. In this case, meridian arcs are utilized. For each processing diameter, the average length of all the meridian arcs is calculated. The processing diameter then becomes the abscissa value, and the average meridian arc length becomes the corresponding ordinate value. After the average meridian arc length has been calculated for a complete set of processing diameters, the curve of FIG. 19 is obtained. It should be noted that the curve in FIG. 19 has a "knee", as indicated. The value of the processing diameter corresponding to that knee is then selected as the diameter for a best fit sphere for the surface model. That sphere will be utilized to generate a modified elevational display of the cornea, a topological display of the difference between the surface model and the best-fit sphere. This topology as represented in different colors that correspond to different corneal depths.

Figure 20:
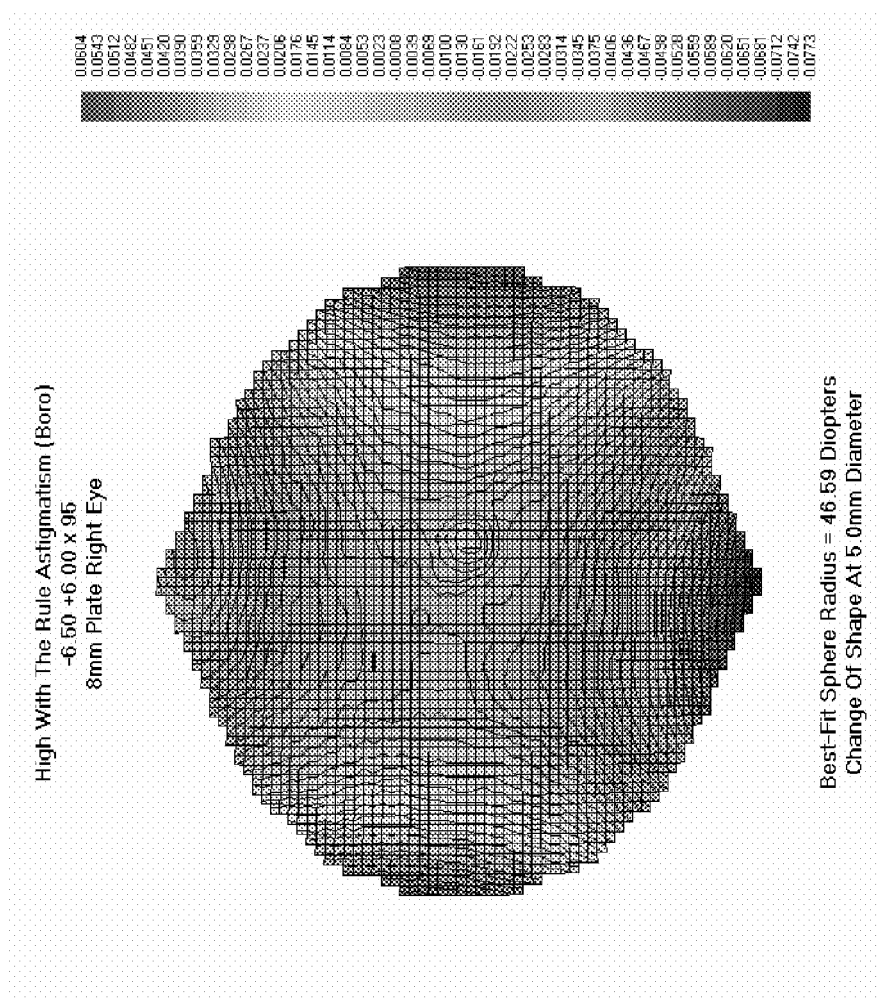
FIG. 20 is a modified elevational display for an astigmatic eye.
Figure 21:
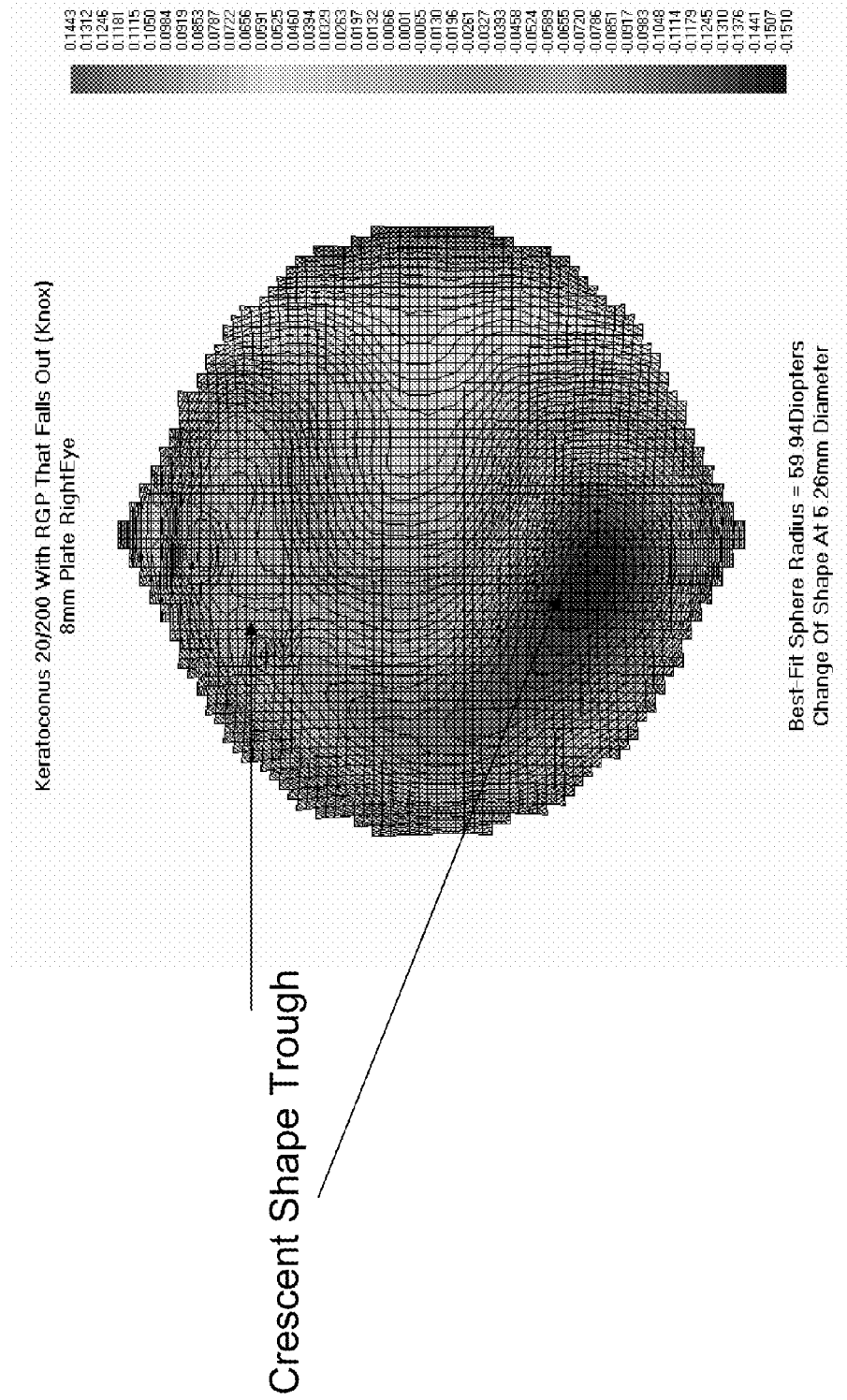
FIG. 21 illustrates the "marker" for a keratoconic eye in accordance with a modified elevational display, which is the presence of a crescent-shaped trough in the elevational display.
Figure 22:
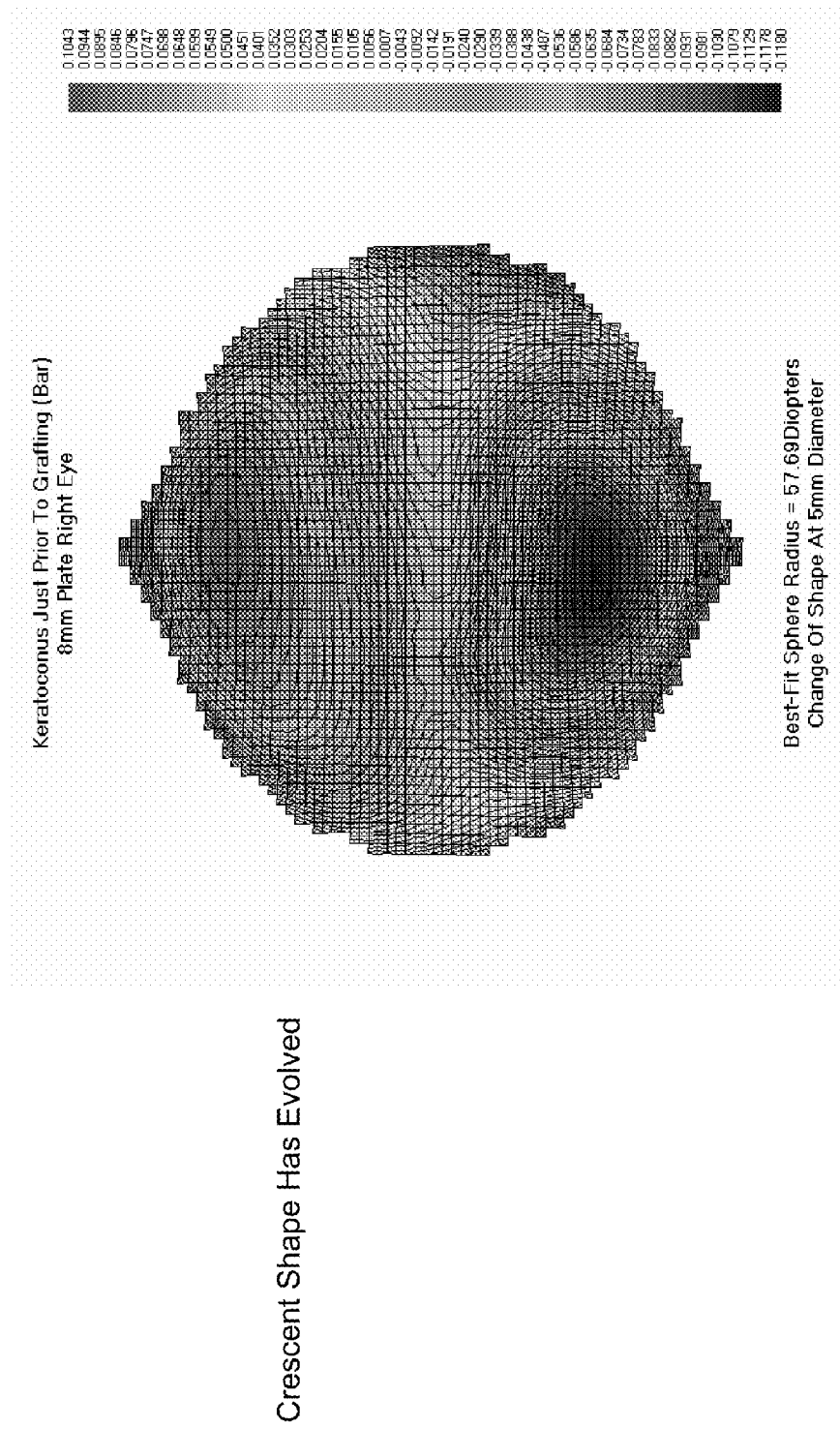
FIG. 22 is a modified elevational display of an eye with advanced keratoconus, the crescent shape having evolved into two separate troughs.

FIG. 20 is an elevational display which is typical for an astigmatic eye. On the other hand, the "marker" for a keratoconic eye is the presence of a crescent-shaped trough in the elevational display, as illustrated in FIG. 21. FIG. 22 is an elevational display of an eye with advanced keratoconus. The crescent shape has now evolved into two separate troughs.

Figure 23:
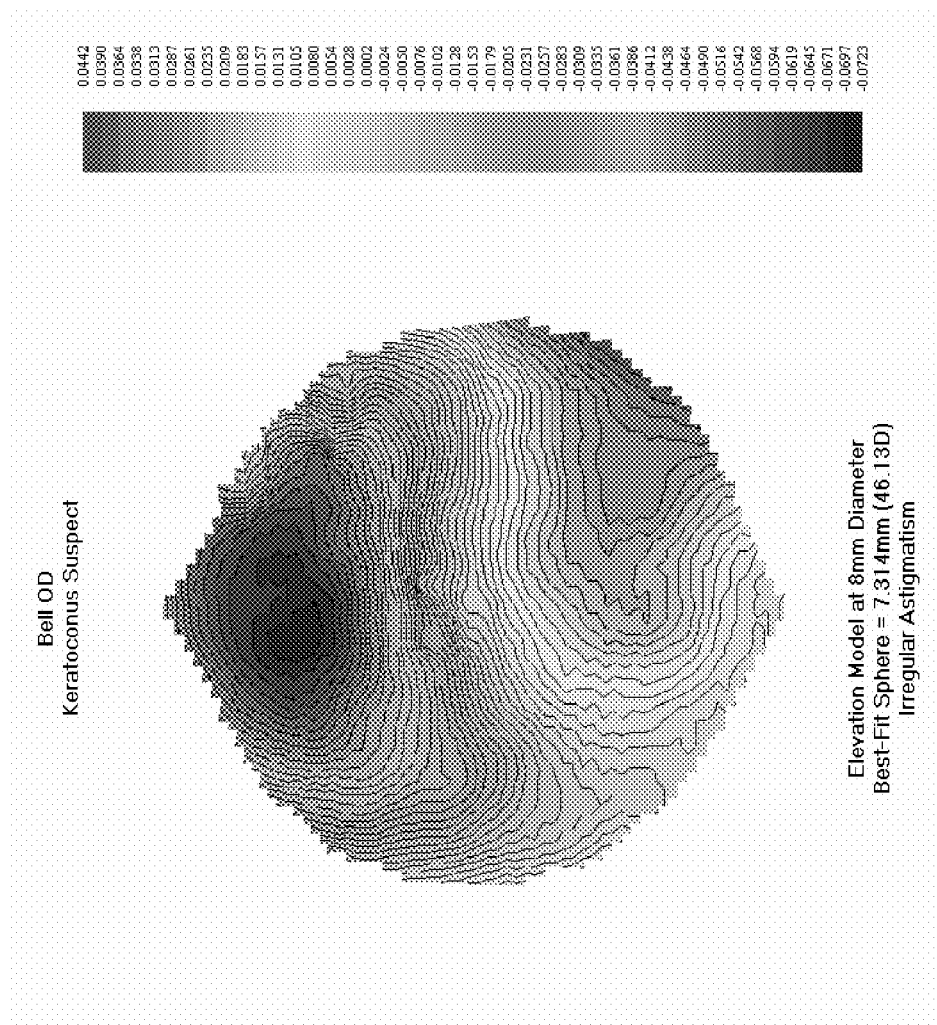
FIG. 23 is customary elevational display (least-squares best-fit sphere) of a keratoconic eye.
Figure 24:
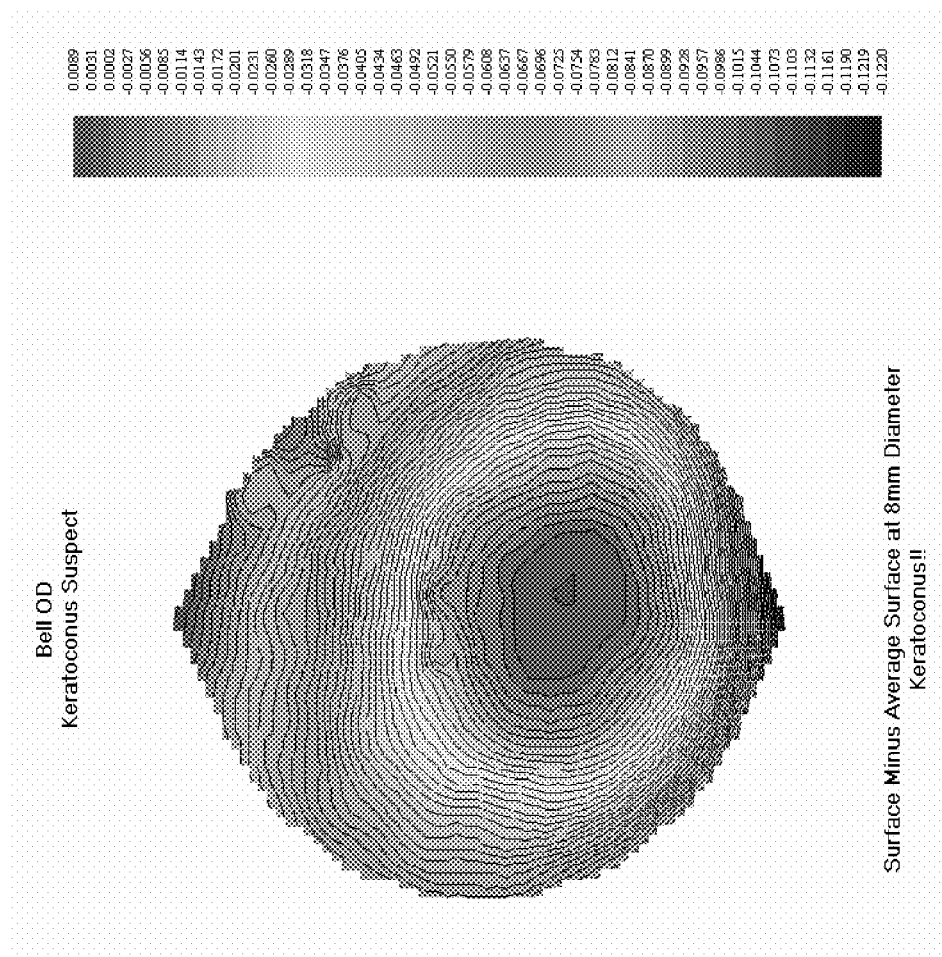
FIG. 24 is a modified elevational display of the same keratoconic eye in accordance with yet another embodiment, this embodiment making use of a best-fit reference surface instead of a sphere, the best fit reference corresponding to a statistically average corneal surface model, determined over a population with excellent, astigmatism-free vision.

As explained above, a customary elevational display shows the topological difference between the surface model and a best-fit sphere. However, experimentation has led us to a modified elevational display, which illustrates the topological difference between the surface model and an average surface model derived from a plurality of normal eyes with 20/20 or better corrected acuity and without refractive astigmatism. FIG. 23 is a customary elevational display of a keratoconic eye (showing a high degree of irregular astigmatism), and FIG. 24 is a modified elevational display, as defined immediately above, of the same eye. While it would be difficult, if not impossible, to determine from FIG. 23 that this is a keratoconic eye, FIG. 24 makes it remarkably evident that there is a red peak and a rapidly rising area around it. Therefore, this is a clear and unmistakable marker for keratoconus.

Figure 25:
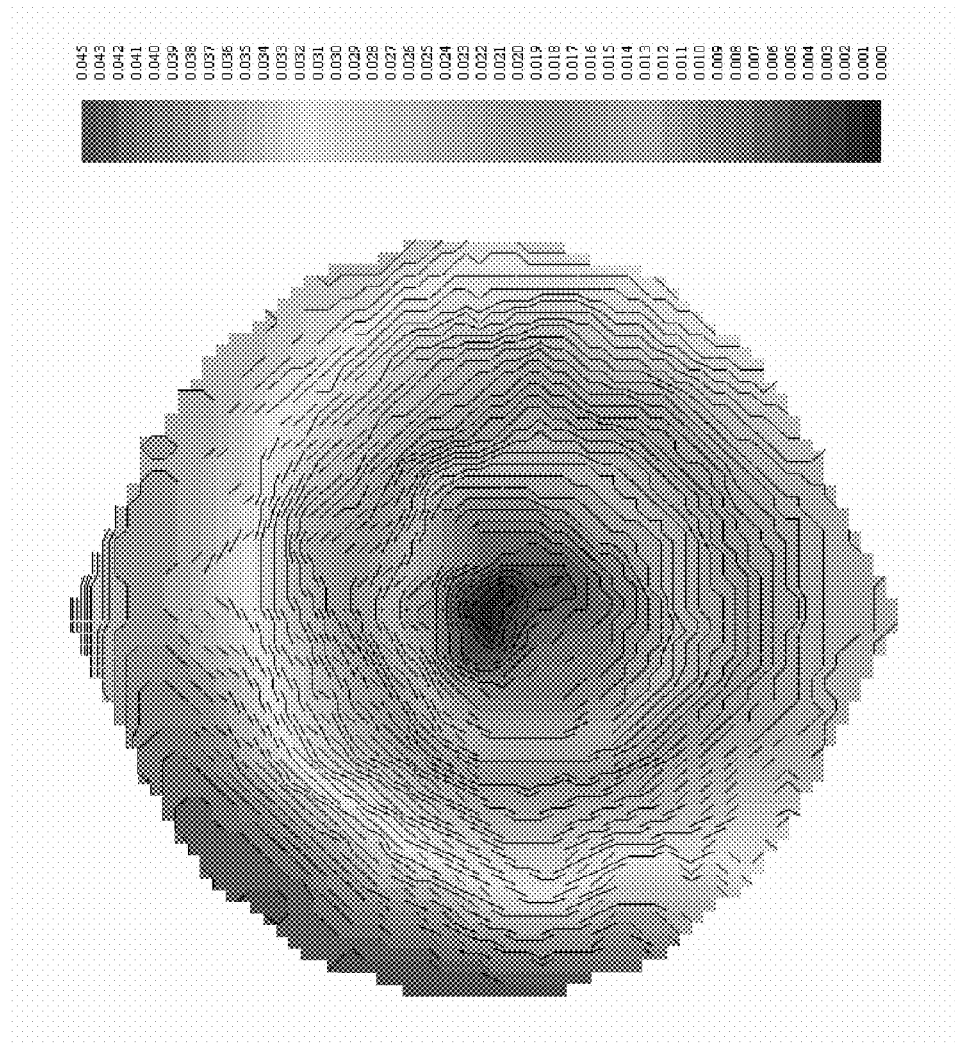
FIG. 25 is a modified elevational display of a patient who has had LASIK surgery and is pleased with the resulting vision.
Figure 26:
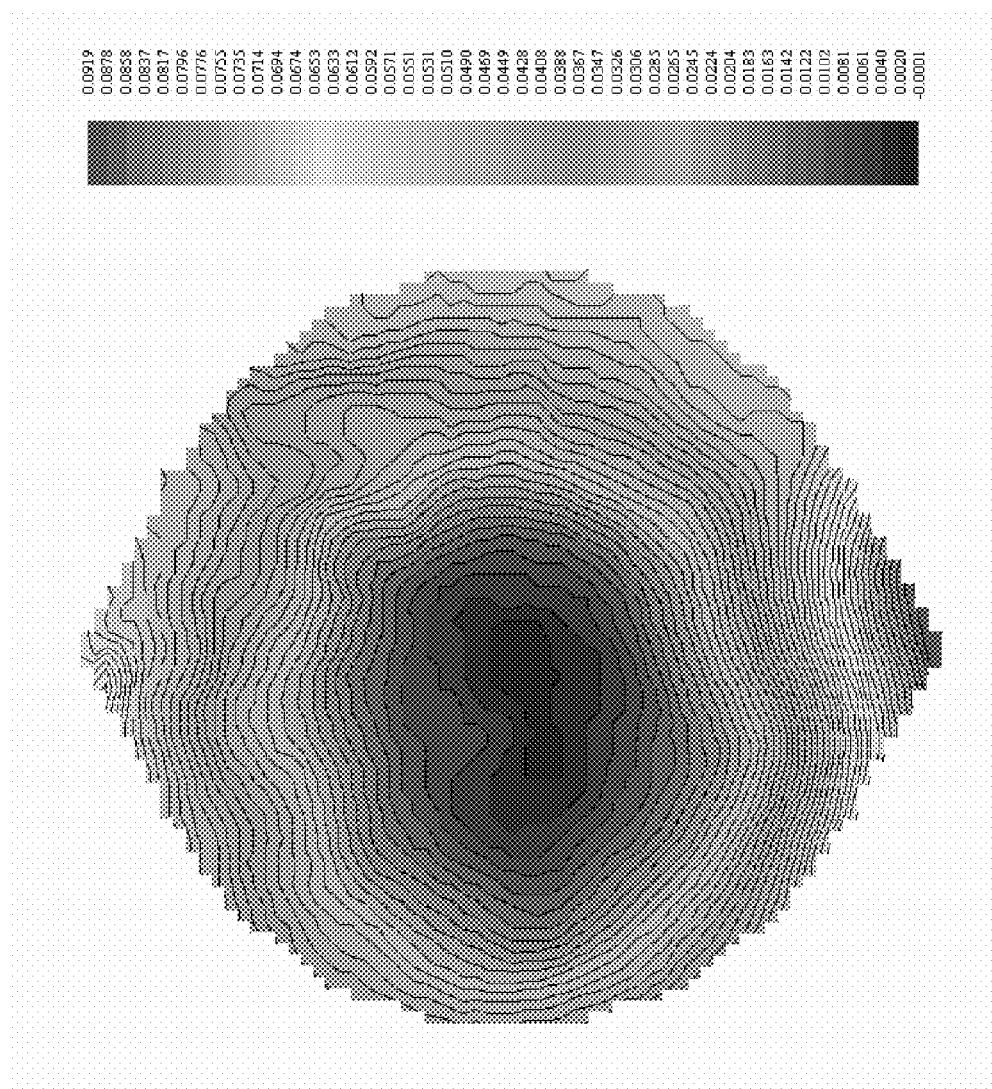
FIG. 26 is a modified elevational display of a patient who has had LASIK surgery and is displeased with the resulting vision.
Figure 27:
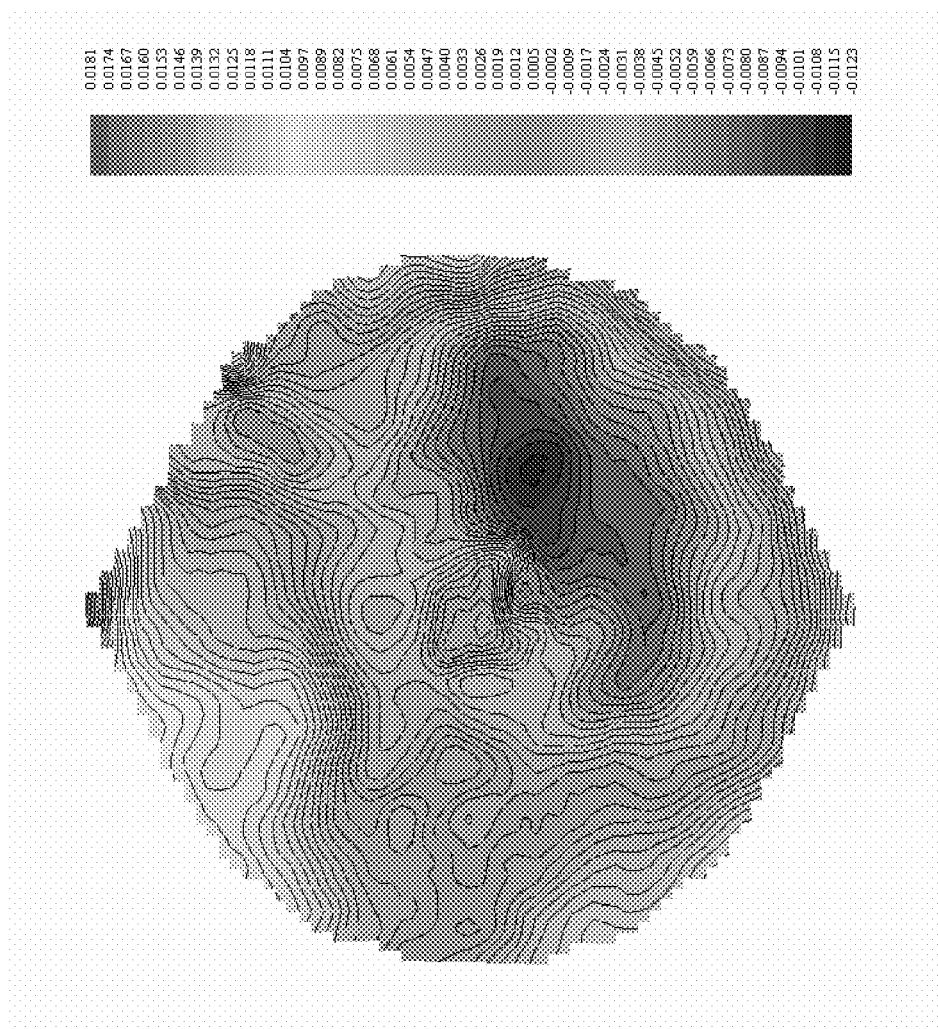
FIG. 27 is a modified elevational display of a patient of a 10 year old patient is a poor reader and has been labeled dyslexic.

FIG. 25 is a modified elevational display of a patient who has had LASIK surgery and is pleased with the resulting vision and FIG. 26 is a modified elevational display of a patient who has had LASIK surgery and is very displeased with the resulting vision. As may be seen, the quality of the vision is related to how well the ablated central region is centered and how well it is localized. Thus it would be possible for a surgeon to "perform" a simulated intended LASIK procedure on the surface model and to predict its effectiveness by analyzing the modified elevational display. If the procedure resulted in a display like FIG. 27, the procedure could be modified until a display similar to FIG. 26 resulted.

FIG. 26 is a modified elevational display of a 10 year old patient who is a poor reader and has been labeled dyslexic. The patient is a simple myope and has 20/20 vision with no refractive astigmatism. However, the modified elevational display indicates that this patient may very well have a correctable vision issue. Thus the modified elevational display not only yields markers for known disorders of the eye, but is also a useful diagnostic tool to uncover and analyze visual disorders where they were not previously suspected.

Forme fruste keratoconus (FFKC) is an early stage of the disease and has long been difficult, if not impossible, to detect reliably using currently available diagnostic techniques. At the same time, it is a condition which seriously degrades the eye structurally, and certain types of surgery, such as LASIK, can lead to disastrous results, with no possibility of restoring normal vision short of a corneal transplant. A reliable test to detect FFKC would therefore be of great value. Although the medical profession has specific definition of FFKC, that term will be used herein to refer to all forms of early keratoconus which have, until now been essentially undetectable.

The Pentacam eye scanner, available from Oculus, Inc., of Lynnwood, Wash., is capable of providing a topographic scan of both the anterior and posterior surfaces of the cornea. In order for these scans to be useful for the creation of corneal models, the scan data had to be modified. The Pentacam produces a set of sample points referenced to the corneal apex. The center of the Pentacam grid is about a "center of rotation" and the apex or High Point is located somewhere else within the point cloud. To produce a model, the set of points was transformed so as to be referenced to the HIGH point. In addition, the set of points was processed as described in copending U.S. application Ser. No. 60/829,030 to remove the effects of any residual tilt that may be present in a model produced from the set of points. This resulted in a much more accurate and reliable surface model.

For purposes of further discussion, it will be assumed that the surface model is defined in a three-dimensional coordinate system, in which the z-axis corresponds to the depth of the cornea and the x and y axes lie in the reference plane of the scanner or a plane parallel to it. A "top-down" view will be understood to be a view of the x-y plane when looking along the z-axis. Also angular positions on the cornea will be understood to be top-down, with the zero position being at the nose and angle increasing upward, so that angle 90° represents the superior portion of the cornea and angle 270° represents the inferior portion of the right eye. The same reference system is used for the left, placing 180° at the nose.

Our experimentation has demonstrated that a surface model of the posterior surface of the cornea can be invaluable in detecting FFKC, something that was not possible until now. Apparently the development of keratoconus begins on the posterior surface. Moreover reliability of detection is greatly improved by measuring multiple characteristics of that model, which serve as markers for FFKC. For example: the rate of change of curvature of the bottom of the cornea posterior with increasing distance from the HIGH point; the half-meridian radius of the bottom of the cornea posterior with increasing distance from the HIGH point; and the appearance of an elevational display of the posterior of the cornea.

Figure 28:
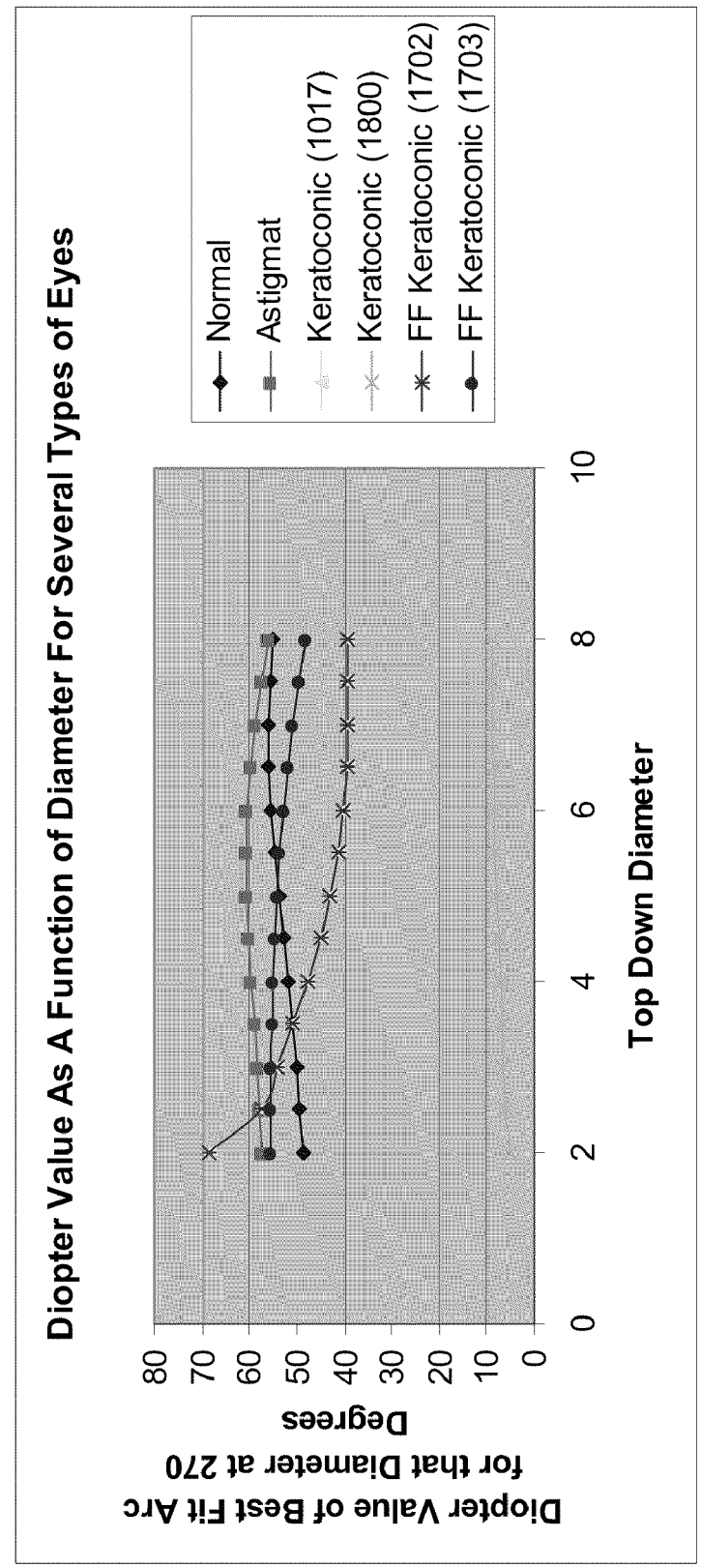
FIG. 28 is a graph of the curvature of the posterior surface of the cornea at angle 270° (in diopters) as a function of the top-down diameter of regard for six different eyes.

FIG. 28 is a graph of the curvature of the posterior surface of the cornea at angle 90° (in diopters) as a function of the top-down distance from the HIGH point (diameter of regard or diameter of the top-down circle). Representative curves for several different types of eyes are shown, including a normal eye, and astigmatic eye, two eyes clinically diagnosed with keratoconus, and two eyes having FFKC. At each diameter of regard, for each eye, the half meridian to the HIGH point was estimated by a circular arc passing through the point at angle 90°, the HIGH point, and the top-down midpoint between these two points on a line extending along the surface of the cornea between the high point and the point on the circle of regard. The radius of this arc was taken as the estimate of the radius of curvature, and the equivalent in diopters was used as the ordinate in FIG. 28.

Figure 29:
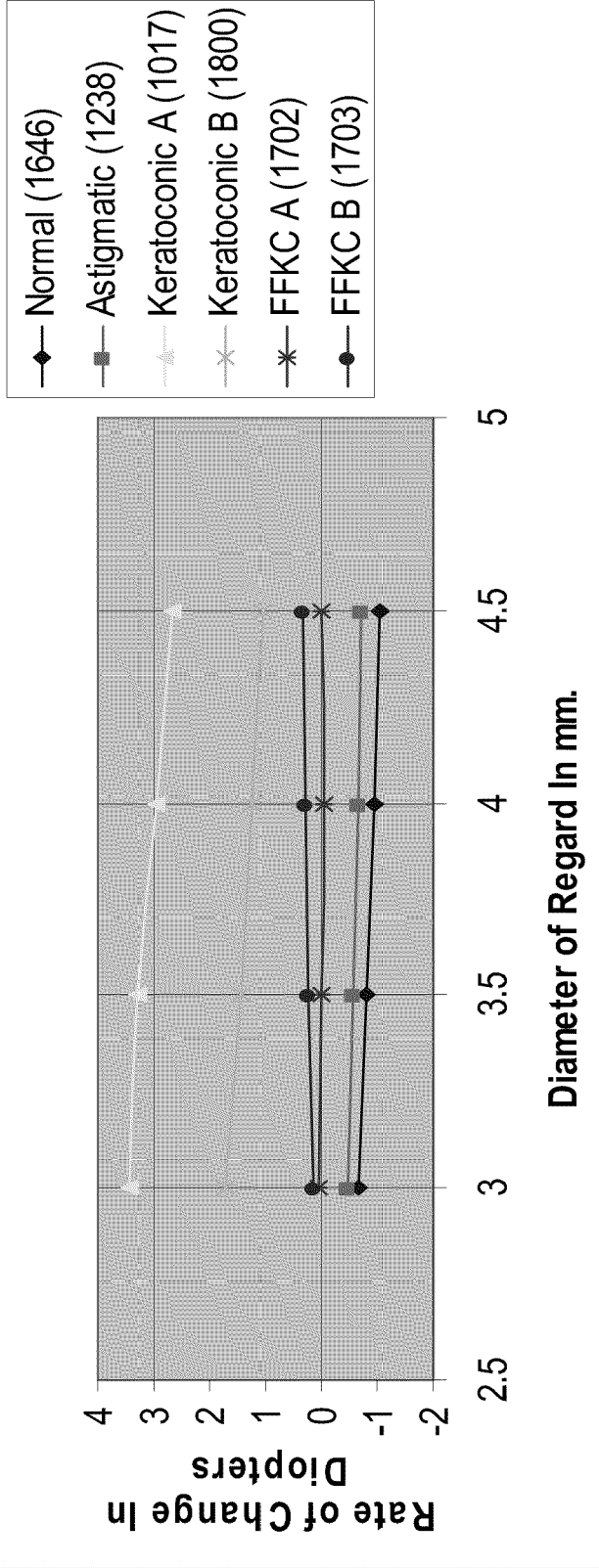
FIG. 29 is a graph of the rate of change of curvature (in diopters) of the posterior surface of the cornea as a function of diameter of regard for each curve illustrated in FIG. 28.

FIG. 29 is a graph of the rate of change of curvature (in diopters) of the posterior surface of the cornea as a function of diameter of regard for each curve illustrated in FIG. 28. It was obtained by measuring the change in curvature of each curve every 0.5 mm of diameter of regard. As a convention, a decrease in curvature was considered to be a positive change.

Figure 30:
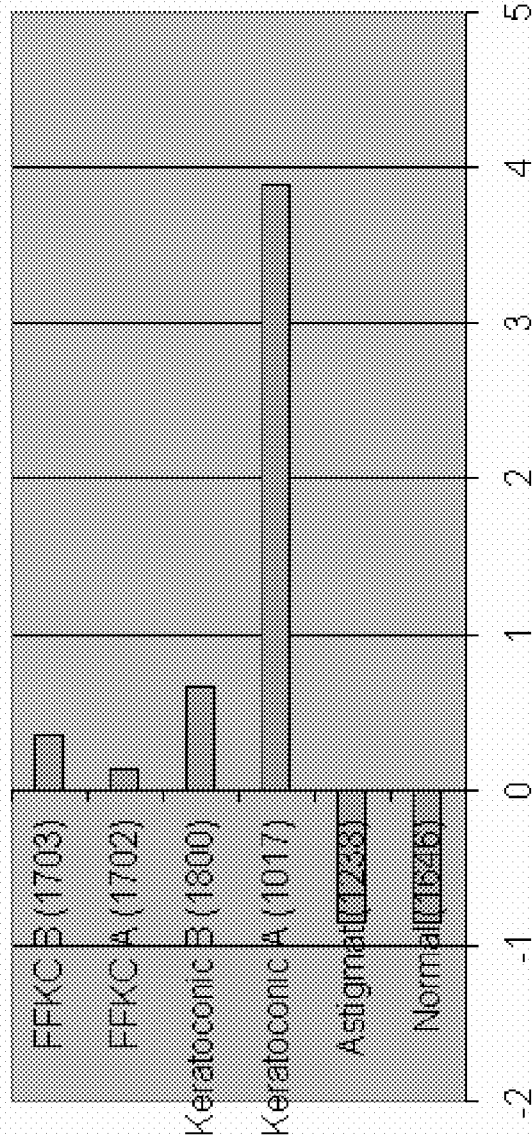
FIG. 30 is a bar graph derived from FIG. 29 illustrating the average rate of change of diopters over the first 5 mm along the posterior cornea surface for each of the curves in FIG. 28.
Figure 31:
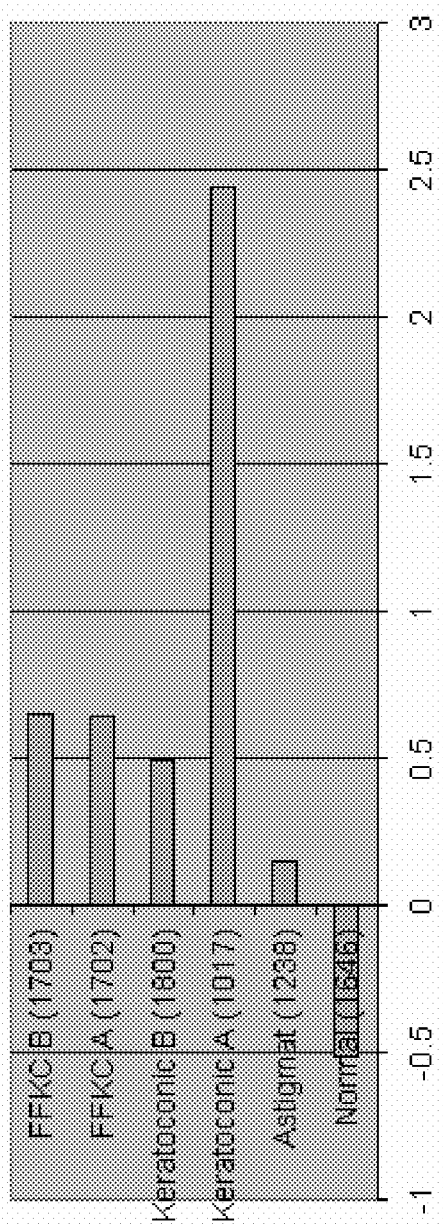
FIG. 31 is a bar graph similar to FIG. 30 showing the average rate of change of diopters over the entire corneal surface from the HIGH point to the outermost most extent of the cornea.

FIG. 30 is a bar graph derived from FIG. 29 illustrating the average rate of change of diopters over the first 5 mm along the posterior cornea surface for each of the curves in FIG. 28, and FIG. 31 is a similar graph showing the average rate of change of diopters over the entire corneal surface from the HIGH point to the outermost extent of the cornea. In all three curves, the rate of change was calculated as a change in instantaneous radius of curvature (measured in diopters). These curves illustrate that the posterior surfaces of normal and astigmatic eyes will have a central portion of the cornea in which the average rate of change of diopters is negative, while keratoconic and FFKC eyes have an average rate of change which is positive. Thus, an FFKC eye can be distinguished from a normal or astigmatic eye.

For a second characteristic, another measurement was taken while advancing vertically downward from the HIGH point (i.e. along axis 270°). At each measurement point, the half-meridian from the HIGH point to the point of measurement (to the diameter of regard) was estimated by a circular arc. The circular arc was drawn through three points: the HIGH point, the point of measurement, and the point halfway between them in the x-y plane. The radius of that arc was converted to diopters and is the value of the ordinate in FIG. 32.

Figure 32:
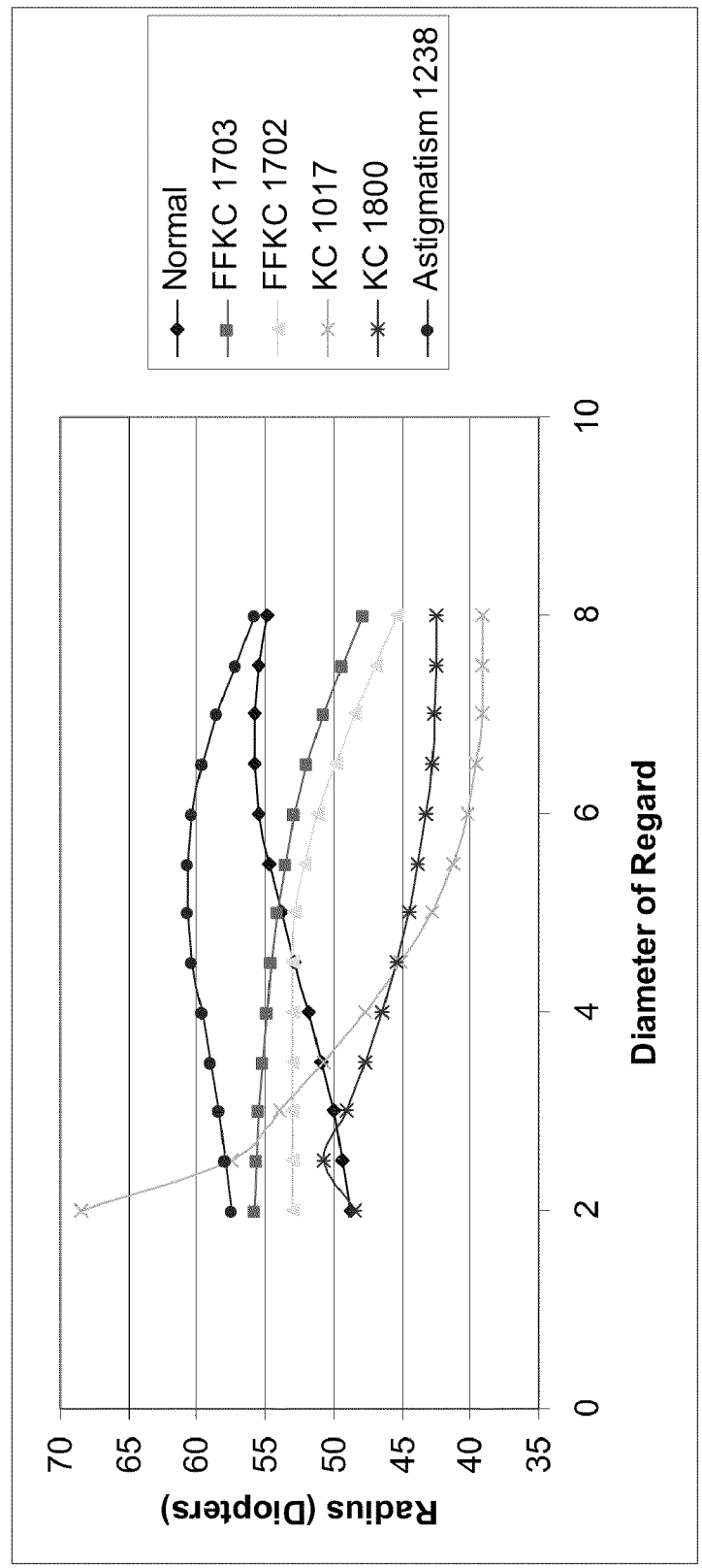
FIG. 32 is a plot, for the same eyes as FIG. 28-31, of curvature (in diopters) as a function of diameter of regard.

FIG. 32 is a plot, for the same eyes as FIG. 28-31, of curvature (in diopters) as a function of diameter of regard. As demonstrated above, keratoconic eyes become more oblate (flatter) with increasing diameter of regard. Normal eyes become more prolate (steeper curvature) with increasing diameter of regard. Astigmatic eyes become increasingly prolate up to about a 5 mm diameter, after which they become more oblate. On the other hand, FFKC eyes are distinguishable in that they are relatively constant in shape up to about a 5 mm diameter, after which they become more oblate. An FFKC eye is therefore distinguishable from a normal eye or an astigmatic eye.

A third characteristic for diagnosing forme fruste keratoconus is derived from topological analysis of the cornea model, specifically from analysis of the elevation display of the posterior surface of the cornea. For this purpose, the best-fit sphere is registered to the surface model at the HIGH point. This computation is done after the surface model is processed to negate the effects of saccadic motion. The elevation display is generated by taking the difference between the surface model and best fit sphere.

Figure 33:
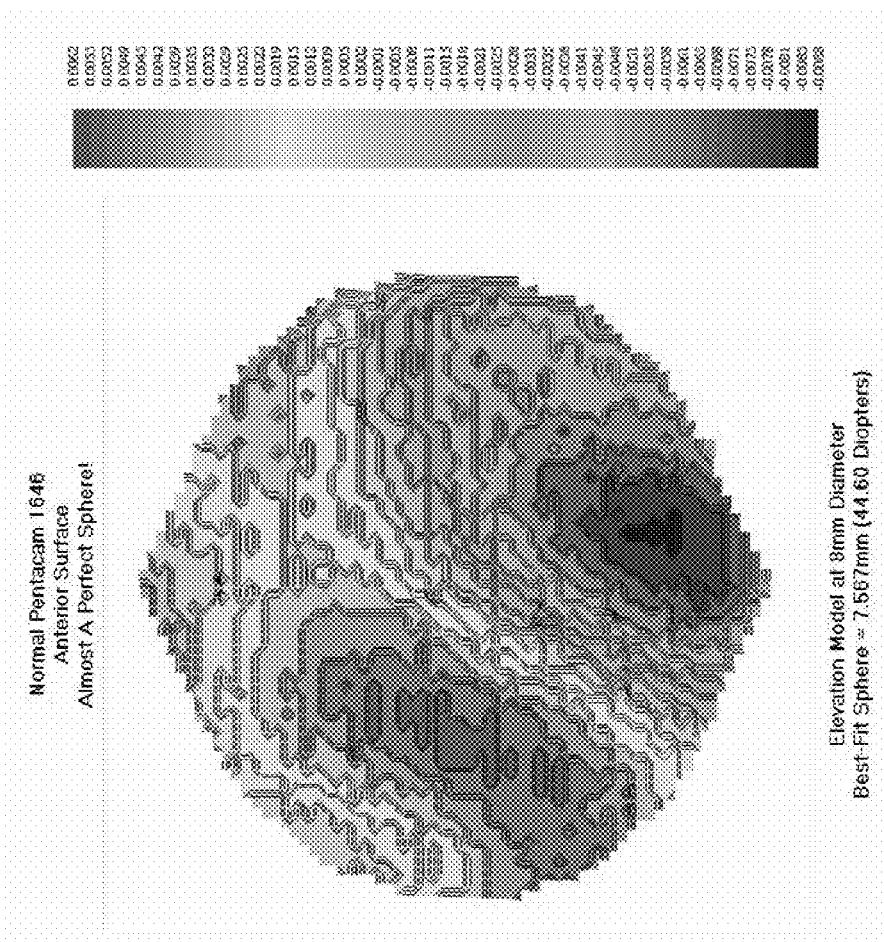
FIG. 33 is an elevational display of the anterior surface of a normal cornea at an 8 mm diameter.

FIG. 33 is an elevational display of the anterior surface of a normal cornea at an 8 mm diameter. From the small values on the scale, it is clear that the anterior surface of a normal cornea is almost a perfect sphere.

Figure 34:
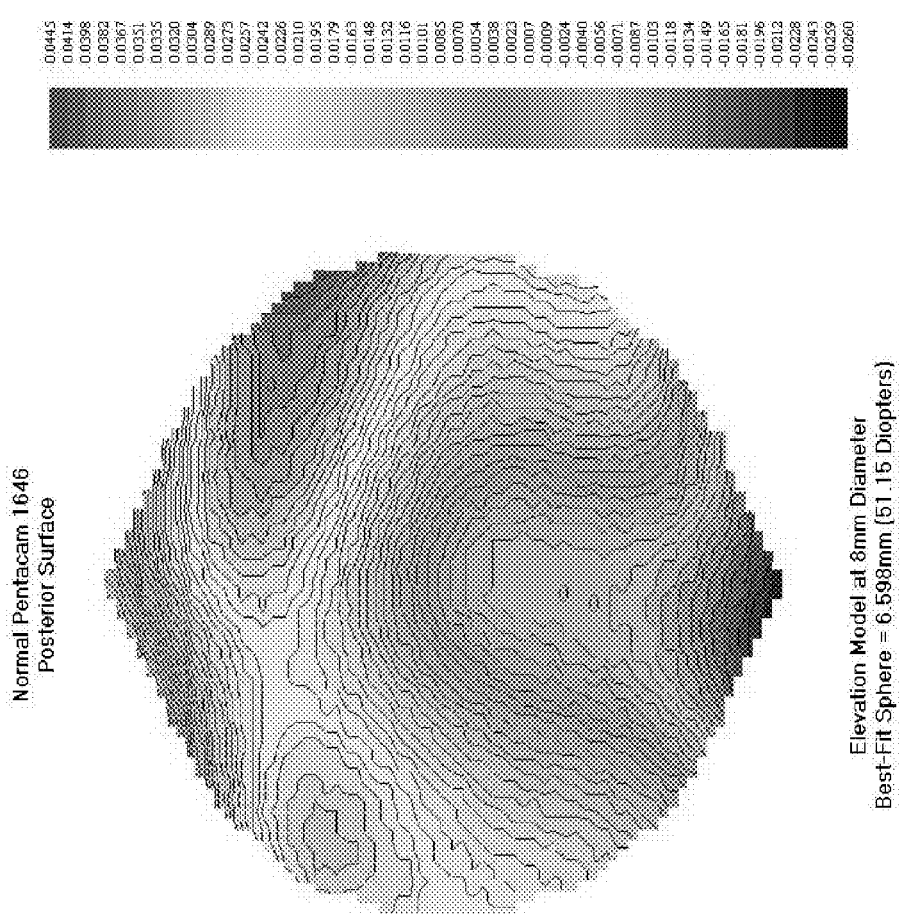
FIG. 34 is an elevational display of the posterior surface of a normal cornea at a diameter of 8 mm.

FIG. 34 is an elevational display of the posterior surface of a normal cornea at a diameter of 8 mm. The posterior surface exhibits far more variation than the anterior surface and does not even approach being spherical.

Figure 35:
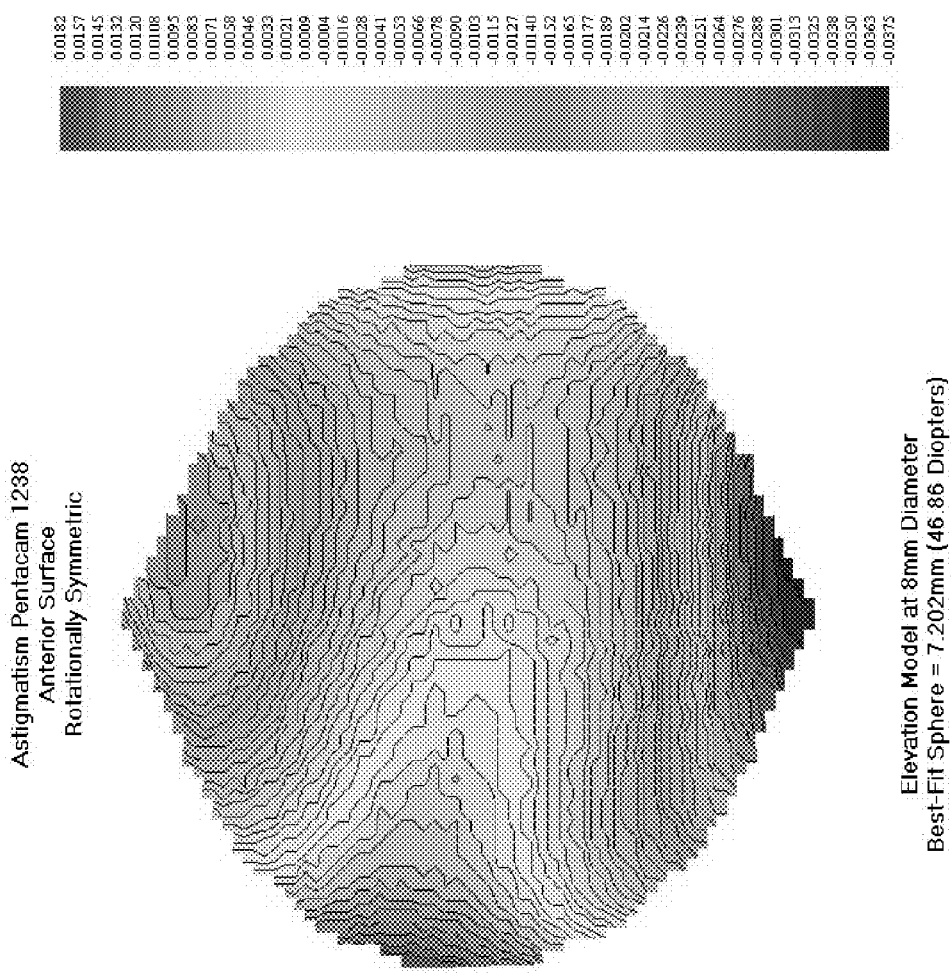
FIG. 35 is a similar elevational display for the anterior surfaces of an astigmatic cornea.
Figure 36:
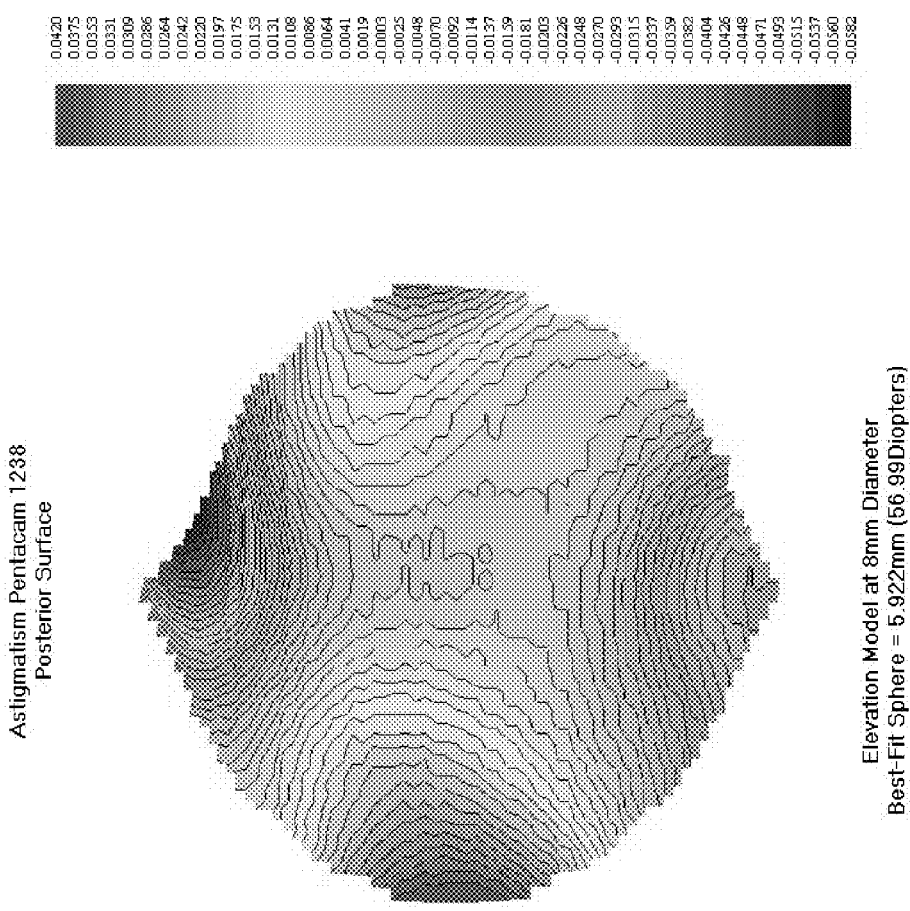
FIG. 36 is a similar elevational display for the posterior surfaces of an astigmatic cornea.

FIGS. 35 and 36 are elevational displays for the anterior and posterior surfaces, respectively, of an astigmatic cornea.

Figure 37:
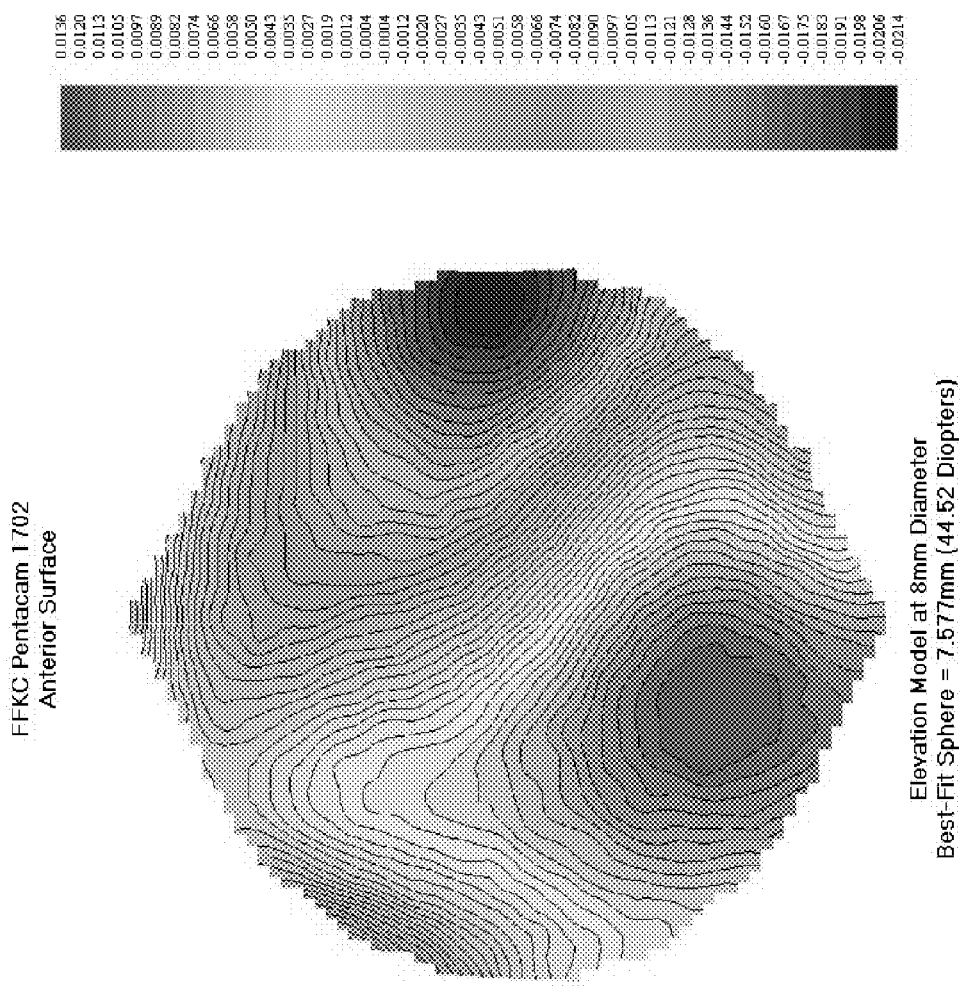
FIG. 37 is an elevational display of the anterior surface, with a diameter of 8 mm, of a cornea inflicted with forme fruste keratoconus, a clinical condition wherein the disease is not yet clinically present.
Figure 38:
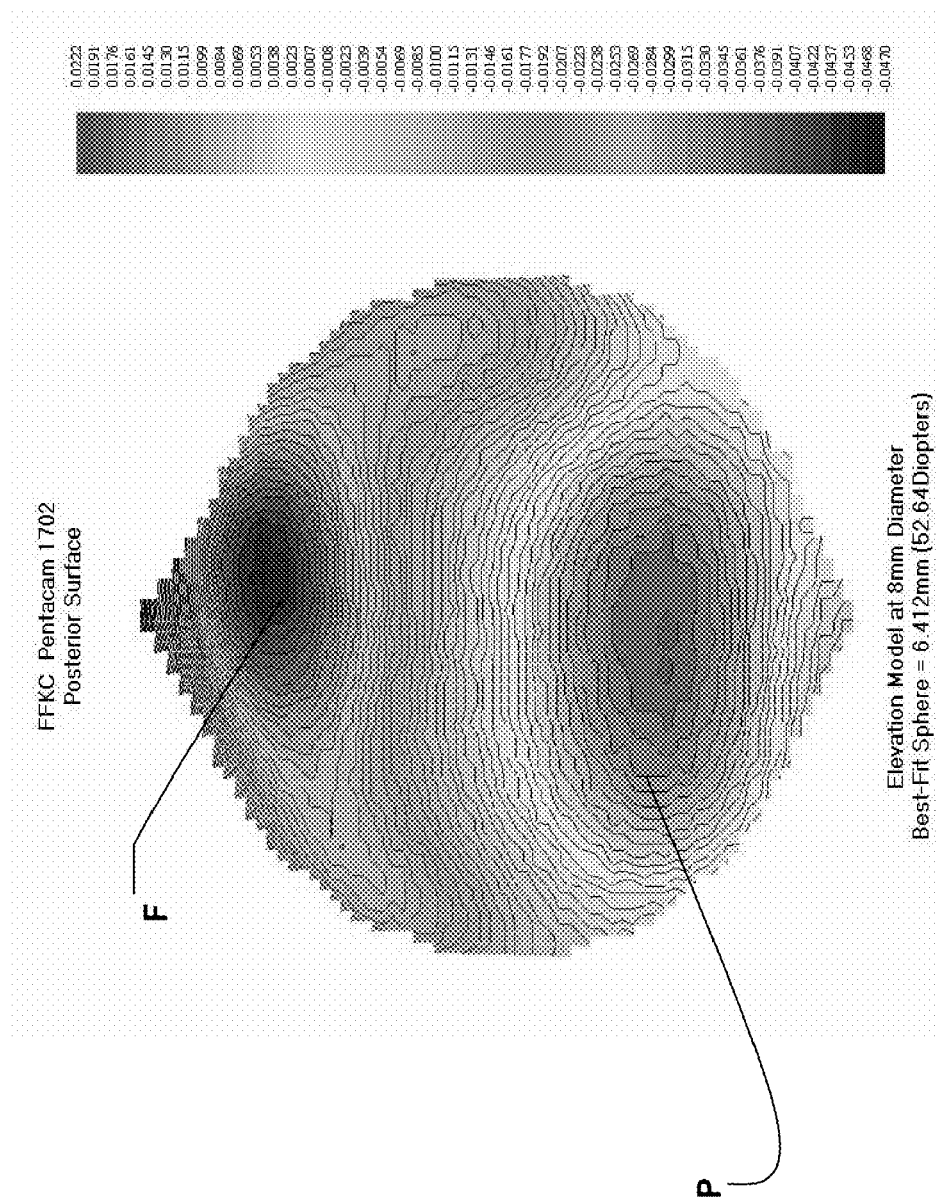
FIG. 38 is a similar elevational display of the posterior surface of a cornea inflicted with forme fruste keratoconus.

FIGS. 37 and 38 are elevational displays of the anterior and posterior surfaces, respectively, with a diameter of 8 mm, of a cornea inflicted with forme fruste keratoconus. It should be noted that the elevational display of the posterior surface exhibits a superior peak (P) at 270°, coupled with an inferior recess or flattening (F) at 90°. This is considered to be a marker for FFKC. The elevational display of the same eye for the anterior surface is shown in FIG. 36. Although it exhibits a peak and a recess, they are not coupled at axis 90° and axis 270°, respectively, as they were for the posterior surface.

It will be appreciated that the marker for FFKC in the elevational view of the posterior surface of the cornea is remarkably distinguishable from similar elevational views of a normal and astigmatic eye. In combination with the two distinguishable markers already described, it can provide a reliable indication of forme frusta keratoconus.

Figure 39:
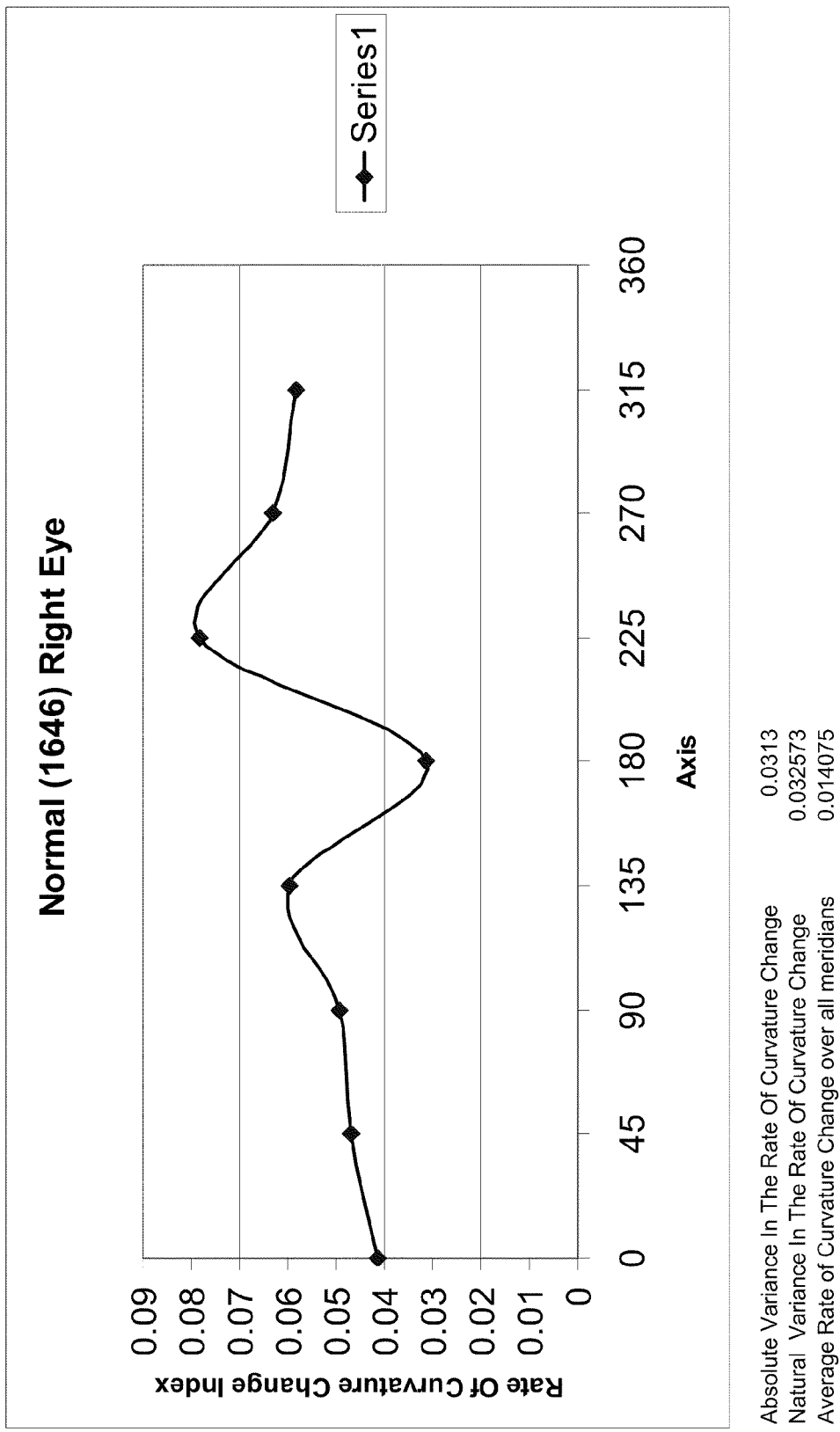
FIG. 39 is a curvature variation plot exemplifying a normal cornea.
Figure 40A:
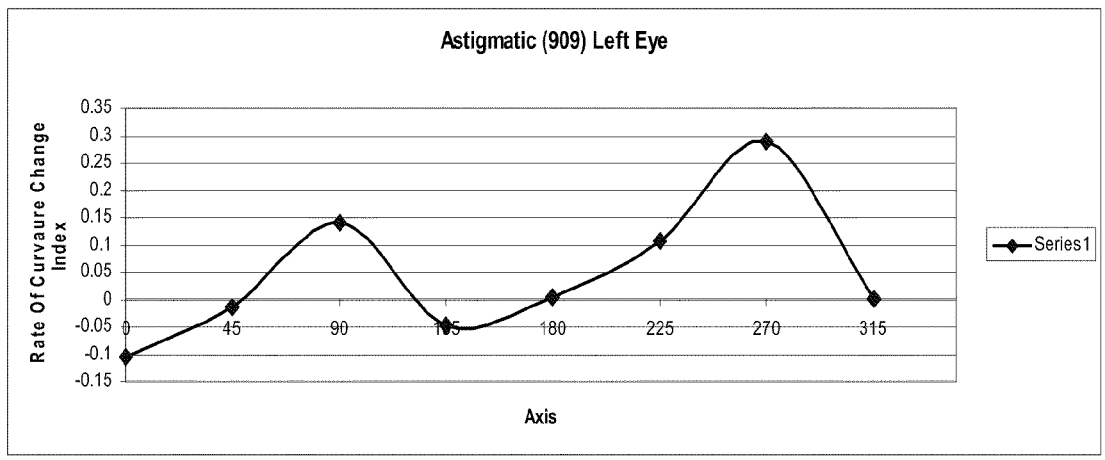
FIGS. 40A and 40B are curvature variation plots exemplifying the corneas of the left and right eyes, respectively of an astigmatic eye.
Figure 40B:
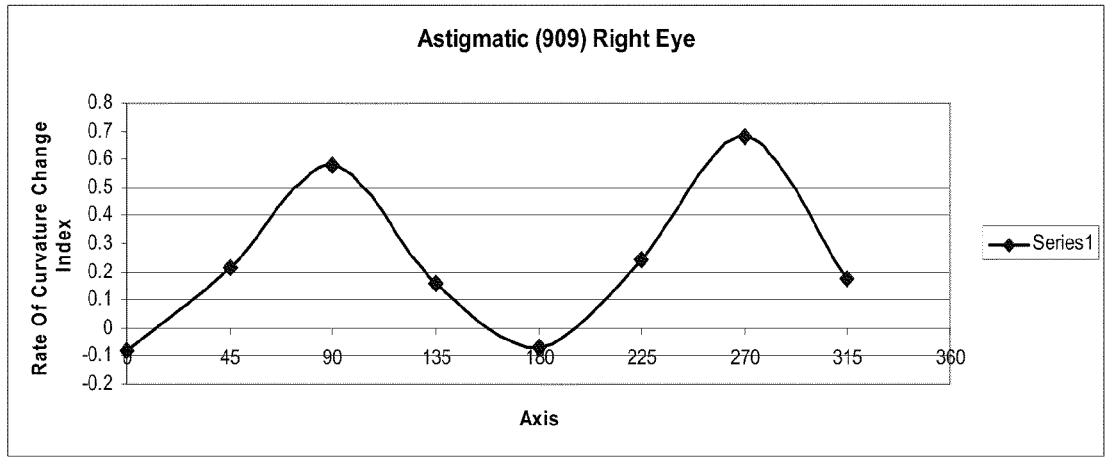
Figure 41A:
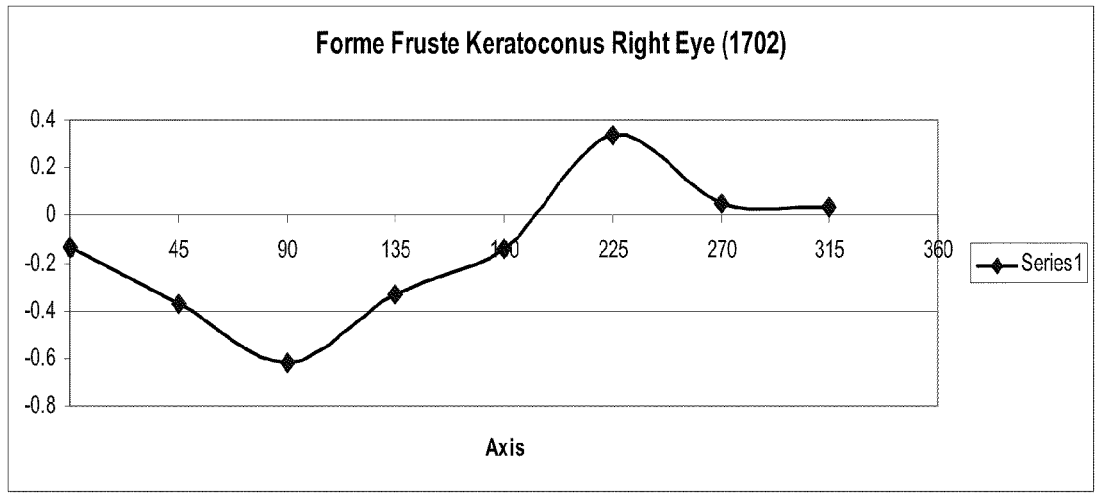
FIGS. 41A and 41B are curvature variation plots exemplifying the corneas of the left and right eyes, respectively of an eye exhibiting the early stages of keratoconus.
Figure 41B:
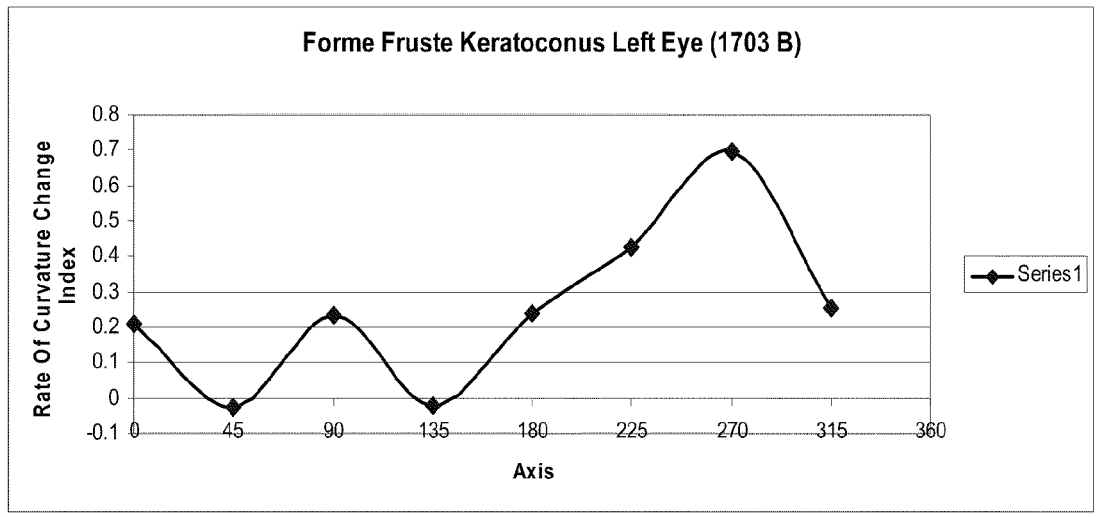

An additional marker has been developed for FFKC which has proven to be reliable and far more sensitive than any of the others. That marker is perceived in the plot of the average rate of change of curvature of half-meridians of the cornea as a function of angular orientation of the half-meridian. All half-meridians pass through the HIGH point and one additional point at the diameter of regard. Half-meridians will be defined in terms of their angular orientation. Where, for the right eye, 0° occurs at the nose and angle increases clockwise. For the left eye, 180° is at the nose. In order to obtain the plot, curvature, preferably in diopters, at at least a set of half-meridians, preferably at a distributed set of ten or more, and the rate of change of curvature is then computed and plotted. That results in a curve such as FIG. 39, which illustrates a rate of change curve for a normal cornea. Similarly, FIGS. 40A and 40B are rate of change curves for the two corneas of an astigmatic, and FIGS. 41A and 41B are similar curves for an FFKC patient. The presently preferred marker occurs in the 45°-225° meridian (the meridian comprising the 45° and 225° half-meridians) for the left eye and the 135°-315° meridian for the right eye. The marker is that the half-meridian at the lower angle has a substantially lower rate of change than the half-meridian at the higher angle. It is also necessary to consider the actual value of the rate of change. A normal cornea exhibits changes in the range of about 0.03 and an astigmatic cornea in the range of about 0.06-0.13, whereas an FFKC cornea exhibits substantially greater changes. Typical FFKC changes are several times that of the largest changes in the astigmatic eye.

Figure 42:
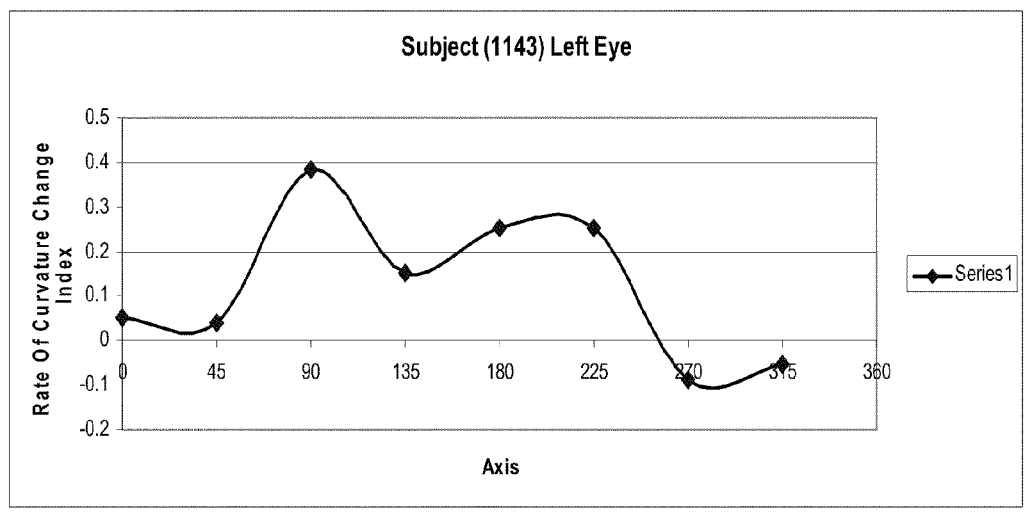
FIG. 42 is a curvature variation plot of the cornea of the left eye of Subject 1143.
Figure 43:
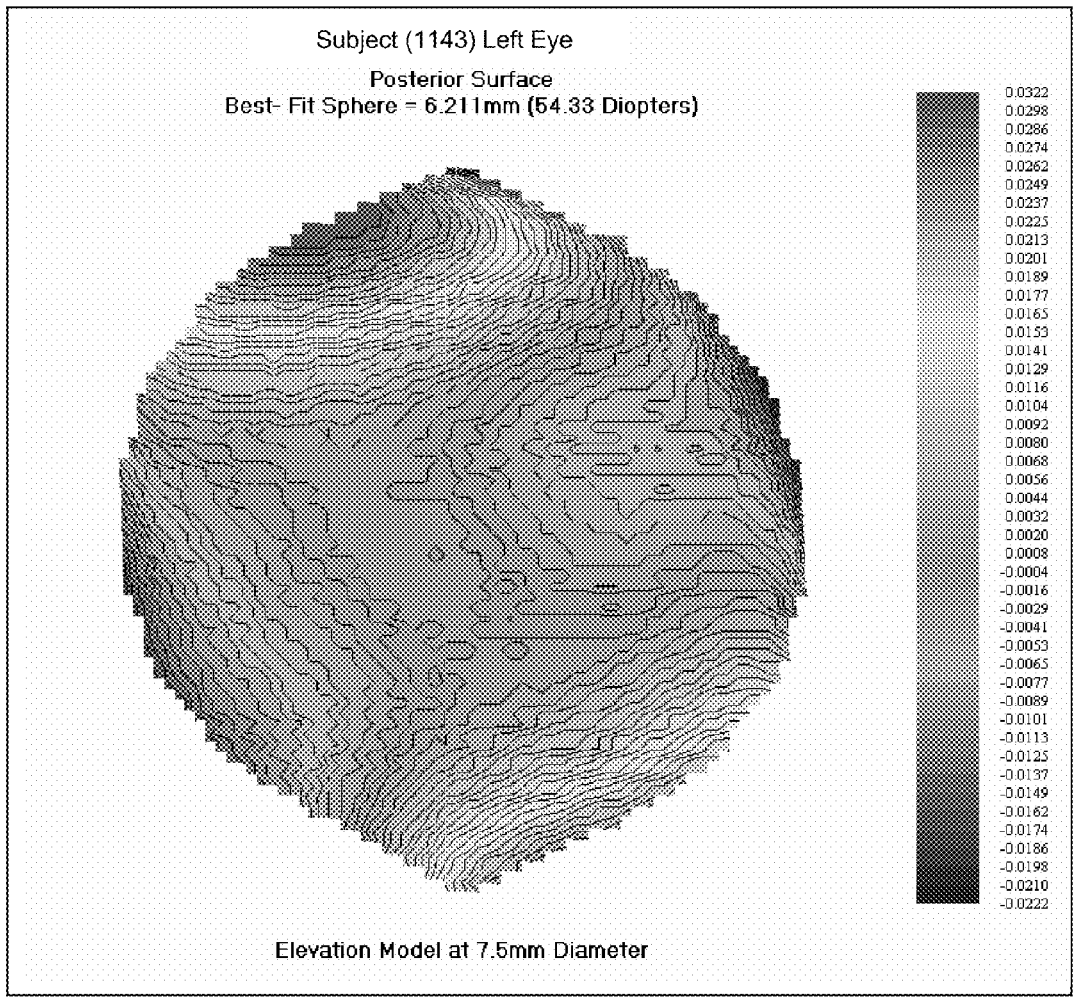
FIG. 43 is an elevational display of the cornea of FIG. 42 at 7.5 mm diameter.

FIG. 42 illustrates the rate of change curve for the left cornea of subject 1143. It clearly exhibits the marker for FFKC. However, the elevational display of the posterior surface of the same cornea (FIG. 43) does not show the marker for FFKC. This demonstrates the superior sensitivity of the rate of change marker.

Although preferred embodiments of the invention have been disclosed for illustrative purposes, those skilled in the art will appreciate that many additions, modifications and substitutions are possible without departing from the scope and spirit of the invention as defined by the accompanying claims.

What is claimed is:

1. A method for performing analysis and diagnosis to establish the presence of maladies of the eye, said method being performed with the aid of a computer system generated surface model of the cornea of the eye which closely represents the surface of the cornea in three dimensions as a smooth, free-form surface, said method comprising the step of manipulating one of the surface model and measurements derived therefrom to create discernable markers that are indicative of a malady of the eye, when present.

2. The method of claim 1 further comprising the steps of:
running a topological modeling computer program on said computer system;
reading into said computer system a file representing sampled points on a topographical measurement of the surface of the cornea of the eye; and
utilizing said file in said computer program to produce said surface model.

3. The method of claim 1 or 2 wherein said manipulating step comprises processing said surface model to derive a parameter of the cornea.

4. The method of claim 3 wherein said manipulating step comprises performing a measurement on said surface model to derive physical measurements of the cornea.

5. The method of claim 1 or 2 wherein said manipulating step comprises analyzing corneal depth of the surface model as a function of radial displacement and treating a substantially constant, substantially greater depth than normal as an indicator of a disorder.

6. The method of claim 5 wherein corneal depth is determined both centrally and peripherally and the presence of substantially constant, substantially greater depth than normal in both instances is treated as a marker for keratoconus.

7. The method of claim 1 or 2 wherein said manipulating step comprises analyzing corneal depth of the surface model as a function of radial displacement over time in order to monitor the progress of a disorder.

8. The method of claim 1 or 2 wherein said manipulating step comprises analyzing the length of lines on the surface model that pass through the HIGH point as a function of their angular orientation and concluding that a disorder exists if the length varies sinusoidally or cosinusoidally with angular orientation.

9. The method of claim 8 wherein line length is determined both centrally and peripherally.

10. The method of claim 8 wherein the line is one of a spline, a meridian and a half-meridian.

11. The method of claim 8 wherein a sinusoidal variation is treated as a marker for keratoconus.

12. The method of claim 8 further comprising performing the analysis as a function of time in order to monitor the progress of a disorder.

13. The method of claim 1 or 2 wherein said manipulating step produces a modified elevational display through the steps, comprising:
 a. selecting a processing diameter of the surface model and generating a plurality of characterizing arcs in the corresponding portion of the surface model;
 b. calculating the average length of all the characterizing arcs;
 c. increasing the processing diameter by a given amount and repeating step b. until a predetermined number of repetitions have been performed to produce a graph of average meridian length as a function of processing diameter, the graph having a knee, the value of the diameter in the vicinity of which is a reference diameter;
 d. generating a modified elevational display representing the difference between the surface model and a sphere having a diameter equal to approximately the reference diameter.

14. The method of claim 13 further comprising concluding that the cornea which is a crescent-shaped trough in the elevational display.

15. The method of claim 13 wherein the surface model is of the posterior surface of the cornea.

16. The method of claim 15 further comprising concluding that the cornea is keratoconic upon the presence of a marker comprising a peak in the lower portion of the display coupled with a recess or flattening in the upper portion of the display.

17. The method of claim 1 or 2 wherein said manipulating step comprises producing an elevational display which is the difference between a surface model of the posterior surface of the cornea and a reference sphere and concluding that the cornea is keratoconic upon the presence of a marker comprising a peak in the lower portion of the display coupled with a recess or flattening in the upper portion of the display.

18. The method of claim 1 or 2 wherein the surface model is of the posterior surface of the cornea.

19. The method of claim 18 wherein said manipulating step comprises measuring the average rate of change of curvature within a diameter of regard on the surface model.

20. The method of claim 18 wherein said manipulating step comprises measuring the average rate of change of curvature as a function of angular orientation on the surface model.

21. The method of claim 20 further comprising considering it a marker for keratoconus when a predetermined relationship exists between the values of average rate of change of curvature at predetermined angular orientations.

22. The method of claim 21 wherein the predetermined orientations for a left eye are 45° and 225°, and the predetermined relation ship is that the rate of change at the latter orientation is higher.

23. The method of claim 22, further comprising requiring the value of rate of change of curvature to substantially exceed 0.1.

24. The method of claim 21 wherein the predetermined orientations for a right eye are 135° and 315°, and the predetermined relation ship is that the rate of change at the latter orientation is higher.

25. The method of claim 24, further comprising requiring the value of rate of change of curvature to substantially exceed 0.1.

26. The method of claim 1 or 2 wherein said manipulating step comprises producing an elevational display which is the difference between the surface model and a reference sphere and concluding that the cornea is keratoconic upon the presence of a marker which is a crescent-shaped trough in the elevational display.

* * * * *